US012788339B2

(12) United States Patent
Zhan et al.

(10) Patent No.: US 12,788,339 B2
(45) Date of Patent: Nov. 10, 2026

(54) DETECTOR RESPONSE CORRECTION METHOD AND APPARATUS FOR A PHOTON COUNTING X-RAY IMAGING SYSTEM

(71) Applicant: Canon Kabushiki Kaisha, Tokyo (JP)

(72) Inventors: Xiaohui Zhan, Vernon Hills, IL (US); Thomas Labno, Vernon Hills, IL (US); Yi Qiang, Vernon Hills, IL (US)

(73) Assignee: Canon Kabushiki Kaisha, Tokyo (JP)

( * ) Notice: Subject to any disclaimer, the term of this patent is extended or adjusted under 35 U.S.C. 154(b) by 146 days.

(21) Appl. No.: 18/789,034

(22) Filed: Jul. 30, 2024

(65) Prior Publication Data

US 2026/0033791 A1 Feb. 5, 2026

(51) Int. Cl.
*A61B 6/42* (2024.01)
*A61B 6/03* (2006.01)
*A61B 6/58* (2024.01)

(52) U.S. Cl.
CPC ............ *A61B 6/4241* (2013.01); *A61B 6/032* (2013.01); *A61B 6/582* (2013.01)

(58) Field of Classification Search
CPC ........ A61B 6/032; A61B 6/4241; A61B 6/582
See application file for complete search history.

(56) References Cited

U.S. PATENT DOCUMENTS 11,249,035 B2 2/2022 Zhan et al.
11,653,892 B2 5/2023 Zhan et al.
11,944,484 B2 4/2024 Zhan et al.
2010/0195804 A1 8/2010 Dafni et al.
2015/0103972 A1 4/2015 Bredmp et al.
2016/0306053 A1 10/2016 Steadman Booker et al.
2017/0086757 A1 3/2017 Rong et al.
2022/0192621 A1 6/2022 Withagen et al.
2022/0296202 A1* 9/2022 Zhan .................... A61B 6/4241

FOREIGN PATENT DOCUMENTS

WO WO-2013008198 A2 * 1/2013 ............. A61B 6/032
WO WO-2024046791 A1 * 3/2024 ............... G06T 5/60

* cited by examiner

*Primary Examiner* — Mark R Gaworecki
(74) *Attorney, Agent, or Firm* — Oblon, McClelland, Maier & Neustadt, L.L.P.

(57) ABSTRACT

A method for performing detector response correction in an X-ray imaging system having a photon-counting detector is disclosed. The method includes obtaining calibration data stored in a calibration data storage, which is generated during a calibration procedure performed with the X-ray imaging system at a first time. The method also includes acquiring air scan data generated through an air scan performed with the X-ray imaging system at a second time after the first time. The method further includes performing, with the X-ray imaging system, an object scan on an imaging object at a third time to generate object scan data. The third time is after the second time. The method further includes performing, using the generated object scan data, detector response correction based on the acquired air scan data and the obtained calibration data, and reconstructing, based on the performed detector response correction, an image of the imaging object.

9 Claims, 13 Drawing Sheets

......

DETECTOR RESPONSE CORRECTION METHOD AND APPARATUS FOR A PHOTON COUNTING X-RAY IMAGING SYSTEM

CROSS-REFERENCE TO RELATED APPLICATIONS

This application is related to U.S. Pat. No. 11,249,035 entitled "TWO-STEP MATERIAL DECOMPOSITION CALIBRATION METHOD FOR A FULL SIZE PHOTON COUNTING COMPUTED TOMOGRAPHY SYSTEM," filed on Jun. 29, 2020 and granted on Feb. 15, 2022; U.S. Pat. No. 11,653,892 entitled "COUNTING RESPONSE AND BEAM HARDENING CALIBRATION METHOD FOR A FULL SIZE PHOTON-COUNTING CT SYSTEM," filed on Jan. 22, 2021 and granted on May 23, 2023; and U.S. Pat. No. 11,944,484 entitled "MATERIAL DECOMPOSITION CALIBRATION METHOD AND APPARATUS FOR A FULL SIZE PHOTON COUNTING CT SYSTEM," filed on Mar. 31, 2021 and granted on Apr. 2, 2024. The contents of the above-identified applications are incorporated herein by reference.

BACKGROUND

Field

The disclosure relates to X-ray Computed Tomography (CT) imaging technology based on a photon counting detector.

Description of the Related Art

Computed tomography (CT) systems and methods are typically used for medical imaging and diagnosis. CT systems generally create projection images through an imaging object's body at a series of projection angles. A radiation source, such as an X-ray tube, irradiates the body of the imaging object and projection images are generated at different angles. Images of the imaging object's body can be reconstructed from the projection images.

Conventionally, energy-integrating detectors (EIDs) and photon-counting detectors (PCDs) have been used to measure CT projection data. PCDs offer many advantages including their capacity for performing spectral CT, wherein the PCDs resolve the counts of incident X-rays into spectral components referred to as energy bins, such that collectively the energy bins span the energy spectrum of the X-ray beam. Unlike non-spectral CT, spectral CT generates information due to different materials exhibiting different X-ray attenuation as a function of the X-ray energy. These differences enable a decomposition of the spectrally resolved projection data into different material components, for example, the two material components of the material decomposition can be bone and water.

Even though PCDs have fast response times, at high X-ray flux rates indicative of clinical X-ray imaging, multiple X-ray detection events on a single detector can occur within the detector's time response, a phenomenon called pileup. Left uncorrected, pileup effects distort the PCD energy response and can degrade reconstructed images from PCDs. When these effects are corrected, spectral CT has many advantages over conventional CT. Various clinical applications can benefit from spectral CT technology, including improved material differentiation since spectral CT extracts complete tissue characterization information from the scanned object.

One challenge for more effectively using semiconductor-based PCDs for spectral CT is performing the material decomposition of the projection data in a robust and efficient manner. For example, correction of pileup in the detection process can be imperfect, and these imperfections degrade the material components resulting from the material decomposition.

In a photon-counting CT system, the semiconductor-based detector using direct conversion is designed to resolve the energy of the individual incoming photons and measure multiple energy bin counts for each integration period. However, due to the detection physics in such semiconductor materials (e.g., CdTe/CZT), the detector energy response is largely degraded/distorted by charge sharing, k-escape, and scattering effects in the energy deposition and charge induction process, as well as electronic noise in the associated front-end electronics. Due to finite signal induction time, at high count-rate conditions, pulse pile-up also distorts the energy response, as discussed above.

Due to the non-uniformity in sensor materials and the complexity of the integrated detection system, it is difficult to accurately model detector responses for a PCD based solely on physics theories or Monte Carlo simulations with certain modeling of the signal induction process, which determines the accuracy of the forward model of each measurement. Moreover, uncertainties in modeling the incident X-ray tube spectrum further introduce additional errors in the forward model. All these factors eventually degrade the accuracy of the attenuation line-integral (for counting mode) or material decomposition accuracy (for spectral mode) derived from PCD measurements, consequently affecting the quality of generated spectral images.

U.S. Pat. Nos. 11,249,035, 11,653,892, and 11,944,484 propose calibration methods for solving similar problems, and use multiple transmission measurements across various known attenuation pathlengths to modify the forward model such that it agrees with calibration measurements. These methods typically use static scans with materials of known thickness, often in rectangular slab shapes.

When compared to conventional EID scintillators, PCD sensor materials often exhibit higher sensitivity to environmental variables such as temperature, humidity, radiation exposure, etc. As a result, it is common for the detector response to gradually drift over time or with usage. Without a proper correction mechanism, this drift can lead to a progressive degradation of image quality, requiring another full calibration using multiple slabs. However, a full calibration procedure is typically time- and labor-intensive. Frequent performance of these recalibrations can significantly disrupt system usage in clinical settings.

Therefore, it is desirable to develop a rapid detector response recalibration or correction approach to maintain the image quality of photon-counting CT systems for as long as possible.

SUMMARY

The present disclosure relates to a method for performing detector response correction in an X-ray imaging system having a photon-counting detector. The method includes obtaining calibration data stored in a calibration data storage. The calibration data is generated during a calibration procedure performed with the X-ray imaging system at a first time. The method also includes acquiring air scan data generated through an air scan performed with the X-ray imaging system at a second time. The second time is after the first time. The method further includes performing, with the X-ray imaging system, an object scan on an imaging object at a third time to generate object scan data. The third time is after the second time. The method further includes performing, using the generated object scan data, detector response correction based on the acquired air scan data and the obtained calibration data, and reconstructing, based on the performed detector response correction, an image of the imaging object.

The disclosure additionally relates to an apparatus for performing detector response correction in an X-ray imaging system having a photon-counting detector. The apparatus includes processing circuitry configured to obtain calibration data stored in a calibration data storage, where the calibration data is generated during a calibration procedure performed with the X-ray imaging system at a first time, acquire air scan data generated through an air scan performed with the X-ray imaging system at a second time, where the second time is after the first time, perform, with the X-ray imaging system, an object scan on an imaging object at a third time to generate object scan data, where the third time is after the second time, perform, using the generated object scan data, detector response correction based on the acquired air scan data and the obtained calibration data, and reconstruct, based on the performed detector response correction, an image of the imaging object.

The disclosure additionally relates to a non-transitory computer readable medium having instructions stored therein that, when executed by one or more processors, cause the one or more processors to perform the above-described method for performing detector response correction in an X-ray imaging system having a photon-counting detector.

Note that this summary section does not specify every embodiment and/or incrementally novel aspect of the present disclosure or claimed invention. Instead, the summary only provides a preliminary discussion of different embodiments and corresponding points of novelty. For additional details and/or possible perspectives of the disclosure and embodiments, the reader is directed to the Detailed Description section and corresponding figures of the present disclosure as further discussed below.

BRIEF DESCRIPTION OF THE DRAWINGS

The application will be better understood in light of the description which is given in a non-limiting manner, accompanied by the attached drawings in which.

DETAILED DESCRIPTION OF THE PREFERRED EMBODIMENTS

The following disclosure provides many different embodiments, or examples, for implementing different features of the provided subject matter. Specific examples of components and arrangements are described below to simplify the present disclosure. These are, of course, merely examples and are not intended to be limiting.

For example, the order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present disclosure can be embodied and viewed in many different ways.

Furthermore, as used herein, the words "a," "an," and the like generally carry a meaning of "one or more," unless stated otherwise.

Figure 1:
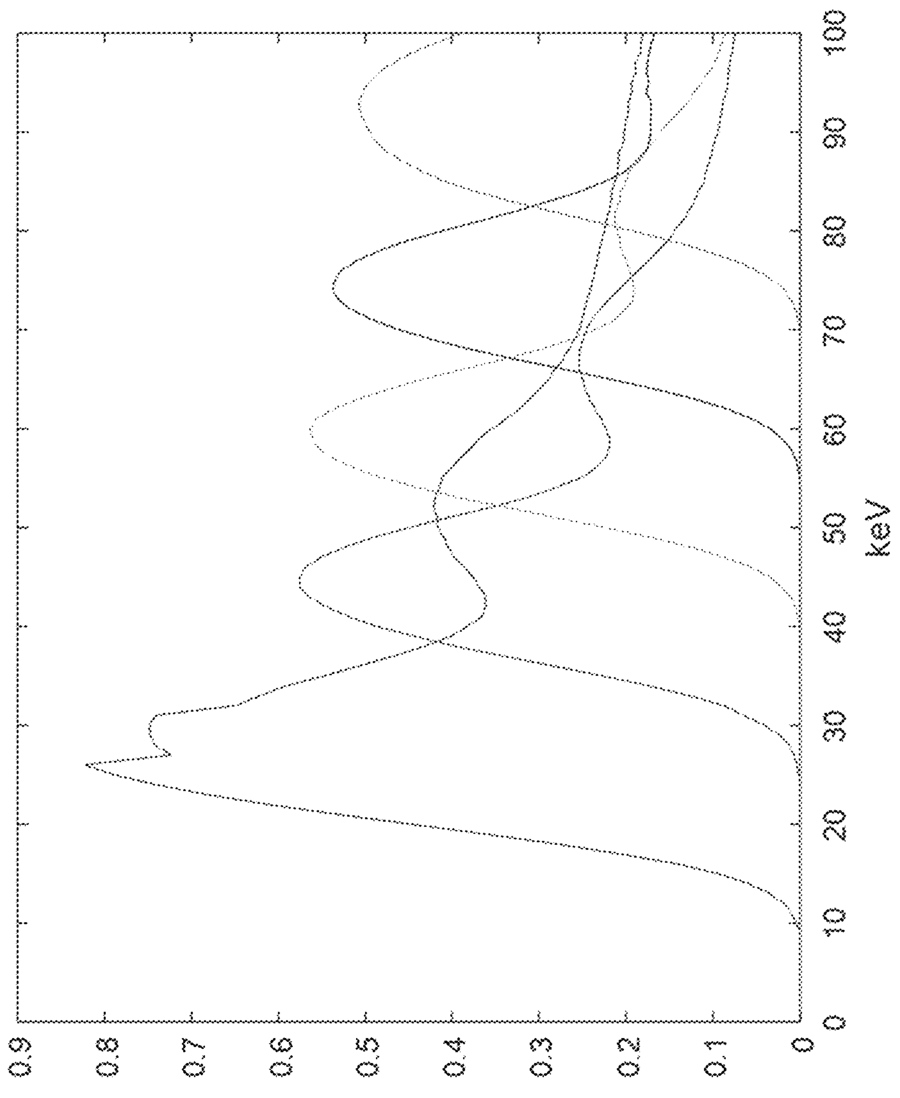
FIG. 1 shows an example of a bin response function $S_b(E)$ for a photon-counting detector (PCD), with each curve standing for an exemplary function for an energy bin.

FIG. 1 shows an example of the bin response function of a photon-counting detector (PCD). As depicted in the figure, due to charge sharing, pulse pileup effects, etc., the bin response function has a very broad distribution beyond the ideal bin energy window for each counter. As mentioned above, U.S. Pat. Nos. 11,249,035, 11,653,892, and 11,944,484 have proposed PCD forward models and calibration methods for both counting and spectral modes. Typically, a calibration procedure can be applied based on multiple transmission measurements of various known attenuation pathlengths to refine the forward model, such that it aligns with calibration measurements.

For example, when the number of the energy bins is n, the PCD forward model can be given by Equation (1):

$$N_{b,j}(b=1,\ \dots\ ,n)=\int_{T_b}^{T_{b+1}}\Phi_b(E')\int_{E_{min}}^{E_{max}}N_{0,j}S_{0,j}(E)D(E,E')e^{\sum_{k=1}^{K}\mu_k(E)l_k}\,dEdE' \tag{1}$$

where E denotes the incident energy, E' denotes the measured energy, $N_{b,j}$ denotes the counts measured at a given detector pixel j for an energy bin b, $\Phi_b(E')$ denotes the binning function which models the function of the data acquisition system (DAS) (or ASIC) that generates digital data indicating counts detected by the detector, $$\Phi_b(E') = \begin{cases} 1, & T_b \leq E' \leq T_{b+1} \\ 0, & \text{others} \end{cases},$$

$T_b$ and $T_{b+1}$ are the low and high energy thresholds of the energy bin b, $E_{min}$ and $E_{max}$ are the low and high energy thresholds of the incident spectrum energy range, $N_{0,j}$ is the incident beam spectrum, which can be represented by the air flux measured at the detector pixel j using an air scan, $S_{0,j}(E)D(E, E')$ is the detector response calibration term ("DR"), and $$\sum_{k=1}^{K} \mu_k(E) l_k$$

is the attenuation sample at the detector pixel j.

As mentioned above, to calibrate the forward model parameters, a set of slab scans using known materials and thicknesses can be conducted. Let $N_{b,i,j}$ be the measured count at the detector pixel j for the energy bin b and a slab i (i=1, . . . , m), the parameters in the PCD forward model can be determined by solving the minimization problem using Equation (2):

$$DR_j^* = \text{argmin}_{DR} \sum_{b=1}^{n} \sum_{i=1}^{m} (y_{b,i}(DR_j) - N_{b,i,j})^2 \quad (2)$$

where $y_{b,i}$ is the counts calculated with respect to the energy bin b, the slab i, and the detector pixel j, with $DR_j$ under a certain air flux $N_{0,j}$ based on Equation (1).

Note that the above equations are designed for the spectral mode of the photon-counting CT. When the photon-counting CT operates under the counting mode, the calculation can be reduced as below:

$$DR_j^* = \text{argmin}_{DR} \sum_{i=1}^{m} (y_{tot,i}(DR_j) - N_{tot,i,j})^2 \quad (3)$$

$$\text{where } y_{tot,i} = \sum_{b=1}^{n} y_{b,i}, \text{ and } N_{tot,i,j} = \sum_{b=1}^{n} N_{b,i,j}.$$

Figure 2A:
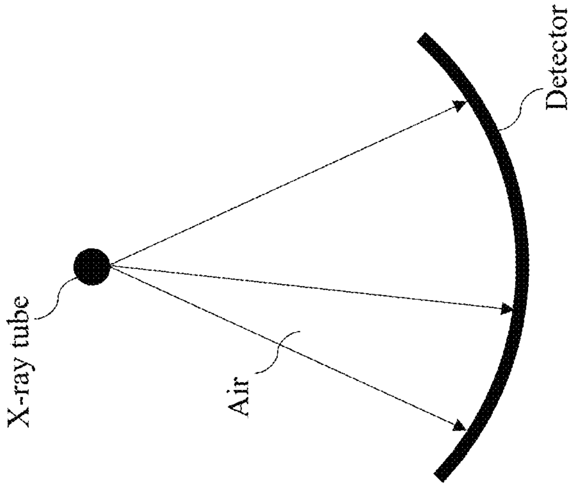
FIGS. 2A-2C show an air scan and slab scans performed during a full calibration procedure, where the slab scans uses different combinations of known materials and thicknesses.
Figure 2B:
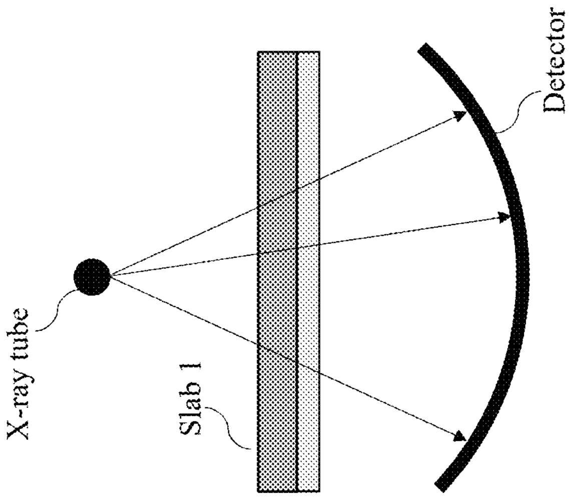
Figure 2C:
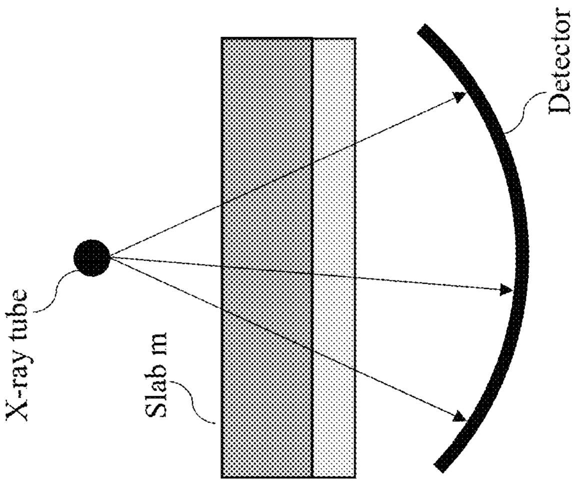

For example, when the PCD calibration scan data is acquired using slabs 1, . . . , m, the procedure generates a set of measurements with the attenuation samples $$att_i = \sum_{k=1}^{K} \mu_k l_k(i),$$

i=1, . . . , m. FIGS. 2A, 2B, and 2C show the air scan and slab scans using different combinations of known materials and thicknesses. In the example shown in FIGS. 2B-2C, the PCD calibration slab scans utilize two basis materials (i.e., K=2), such as solid water/aluminum, or other similar combinations (e.g., iodine, calcium, etc.), to cover an attenuation phase space that would be encountered in object scans. Each of these data points $N_{b,i,j}$ (for the spectral mode; or $N_{tot,i,j}$, for the counting mode) will be used for the cost function calculation.

Typically, when PCD sensor materials undergo a detector response drift, for a given attenuation, the measured bin counts can deviate from the original values obtained during the full calibration. One potential underlying cause for this behavior is the drift of effective energy thresholds from their initial values. As a result, in the previously developed forward model, parameters such as $N_{i,j,b}$ becomes $N_{i,j,b}'$, and $T_{j,b}$ becomes $T_{j,b}'$, for the slab i, the pixel j, and the energy bin b. However, it is difficult to quantify these changes within the system without proper isotope sources. Therefore, when using this altered actual forward model, the original calibration tables are no longer accurate, leading to errors in the line-integral generation of object scans. If the errors reach significant magnitudes, they will cause visible artifacts in the reconstructed object images.

Moreover, sensor materials can experience energy response drifts and detection efficiency changes due to prolonged exposure to X-rays and environmental variables (for example, temperature and humidity fluctuations over time). While the sensor materials may still yield acceptable measurements, they exhibit a shifted response (D(E, E')). To ensure the generation of high-quality images, recalibration of the forward model becomes necessary.

Furthermore, given the potential changes in PCD response, the caused bin count measurement shift can mostly depend on the measured spectrum, which is determined by the beam path attenuation and flux (including pileup effects). Additionally, variations are likely to occur from pixel to pixel, due to material non-uniformity and localized defects.

Therefore, when a typical photon-counting Computed Tomography (PCCT) system is used in clinical settings, how to restore system performance and maintain image quality with minimal downtime is a challenging problem before any substantial material improvements can be made.

The present disclosure provides a method and apparatus for estimating the effective detector response drift and implementing a pixel-by-pixel, energy-bin-by-energy-bin correction, thereby eliminating the need for repeated full calibrations. This approach significantly reduces system downtime, while preserving image quality as much as possible.

To achieve this, the PCD response drift can be captured or monitored through frequent air scans. Then, corrections can be applied to the forward model, using data obtained through the latest air scan, without relying on recalibration procedures that involve measurements across an entire range of attenuation samples.

Figure 3:
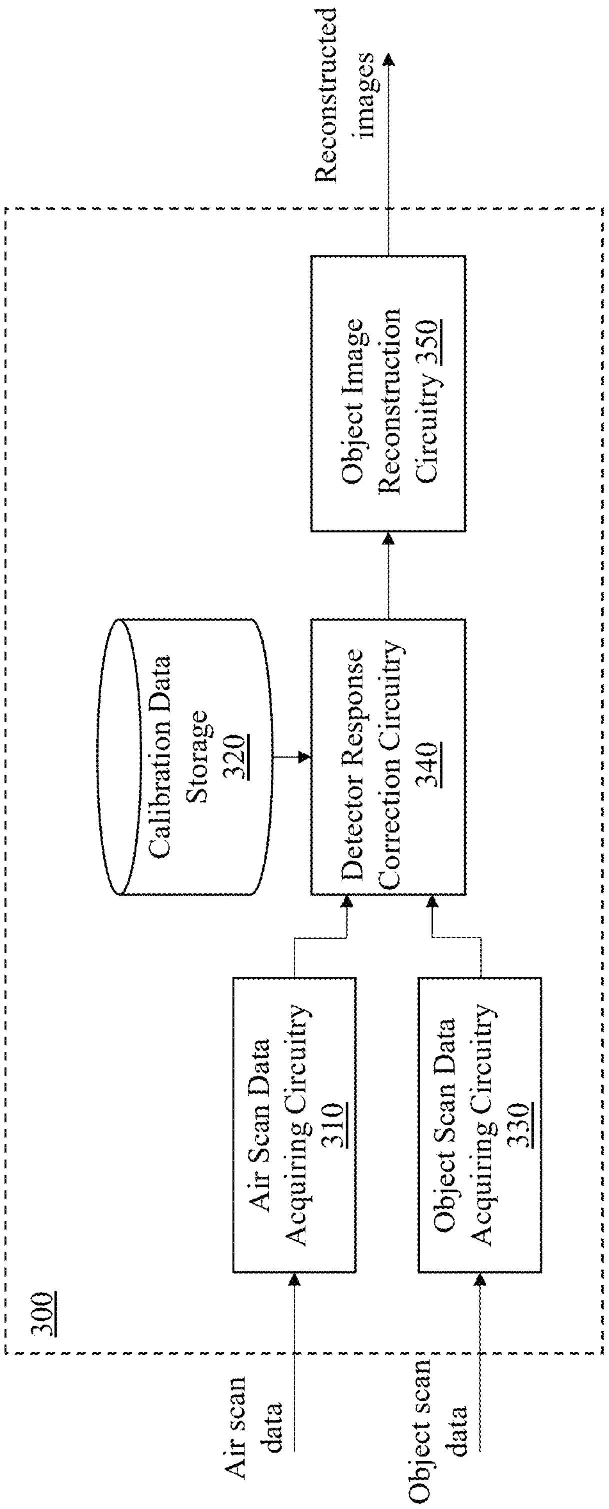
FIG. 3 shows a block diagram of a detector response correction apparatus 300 according to embodiments of the disclosure.

FIG. 3 shows a block diagram of a detector response correction apparatus 300 according to embodiments of the disclosure. The detector response correction apparatus 300 includes air scan data acquiring circuitry 310, calibration data storage 320, object scan data acquiring circuitry 330, detector response correction circuitry 340, and object image reconstruction circuitry 350.

The air scan data acquiring circuitry 310 acquires scan data generated during an air scan, and sends the data to the detector response correction circuitry 340. This air scan can be the most recent one among a plurality of air scans that are regularly or routinely conducted using the PCCT scanner, or can be conducted once a specific criterion is met.

For example, air scans can be scheduled daily, weekly, or monthly. Moreover, an air scan can be triggered when significant variations in operating conditions (such as environmental temperature) of the PCCT scanner are detected, and/or when a different scan protocol (including, but not limited to, the counting mode and the material decomposition mode) is required, etc.

The calibration data storage 320 storages data produced through the full calibration procedure. For example, this data can include calibration air scan data generated from an air scan performed during the full calibration process, and calibration slab scan data obtained from scans conducted on a plurality of slabs during the full calibration. Calibration tables as described in U.S. Pat. Nos. 11,249,035, 11,653,892, and 11,944,484, which are prepared based on the calibration air scan data and calibration slab scan data, are also stored in the calibration data storage 320.

The object scan data acquiring circuitry 330 acquires scan data generated by the PCCT scanner during an object scan of the imaging object, and sends the data to the detector response correction circuitry 340.

Using the calibration data read from the calibration data storage 320 and the latest air scan data received from the air scan data acquiring circuitry 310, the detector response correction circuitry 340 performs detector response correction for the object scan data received from the object scan data acquiring circuitry 330. The function and structure of the detector response correction circuitry 340 will be described below with reference to FIGS. 5-12.

Based on the correction performed by the detector response correction circuitry 340, the object image reconstruction circuitry 350 reconstructs an image of the imaging object.

Figure 4:
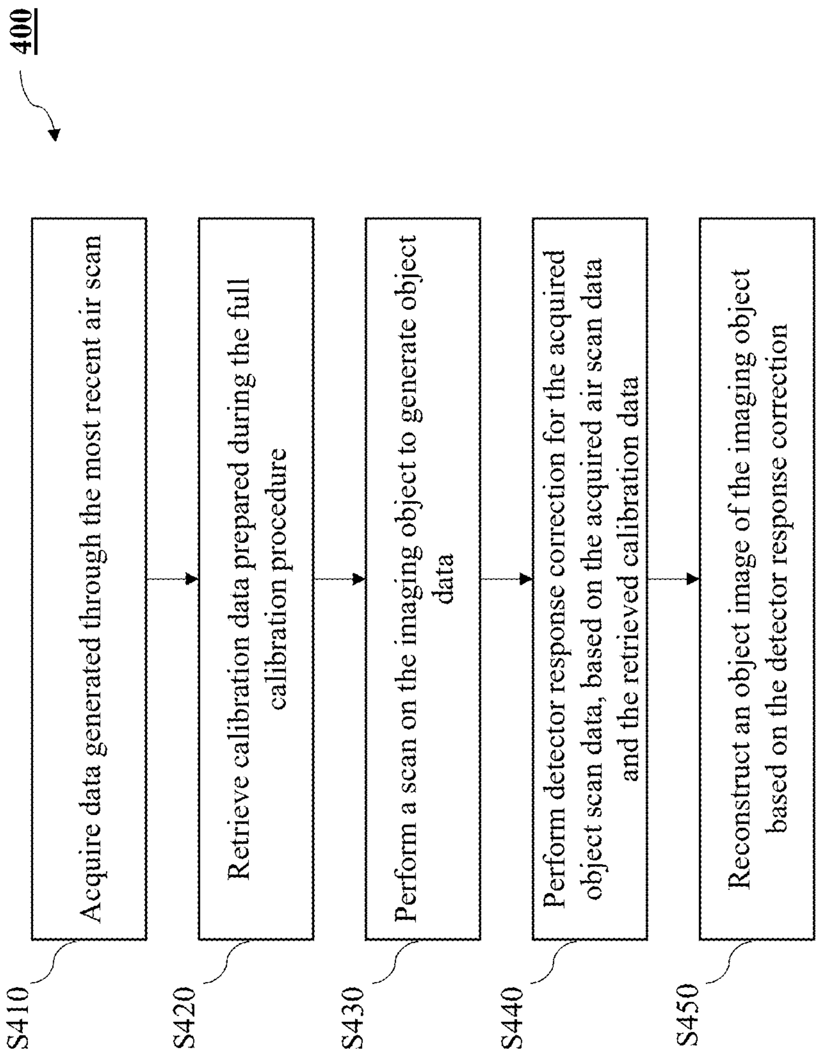
FIG. 4 shows a flow chart of a detector response correction process 400 according to embodiments of the disclosure.

FIG. 4 shows a flow chart of a detector response correction process 400 according to embodiments of the disclosure. In step S410, data generated from the most recent air scan is acquired. In step S420, calibration data prepared during the full calibration procedure is retrieved. In step S430, a scan is conducted with the PCCT scanner on the imaging object to generate object scan data. Then, in step S440, detector response correction is executed with respect to the generated object scan data, using the most recent air scan data and the calibration data. Finally, in step S450, images of the imaging object are reconstructed based on the detector response correction.

According to embodiments of this disclosure, air scan correcting ratios can be determined pixel-by-pixel, energy-bin-by-energy-bin, so as to account for the detector response differences between the original air scan (conducted during the full calibration process) and a new air scan (conducted after the calibration). Then, the correcting ratios can be used to modify the scan data from the object scan, thereby generating adjusted or corrected measurements of the imaging object, as if the PCCT detector is still at its original state when the full calibration is performed.

Figure 5:
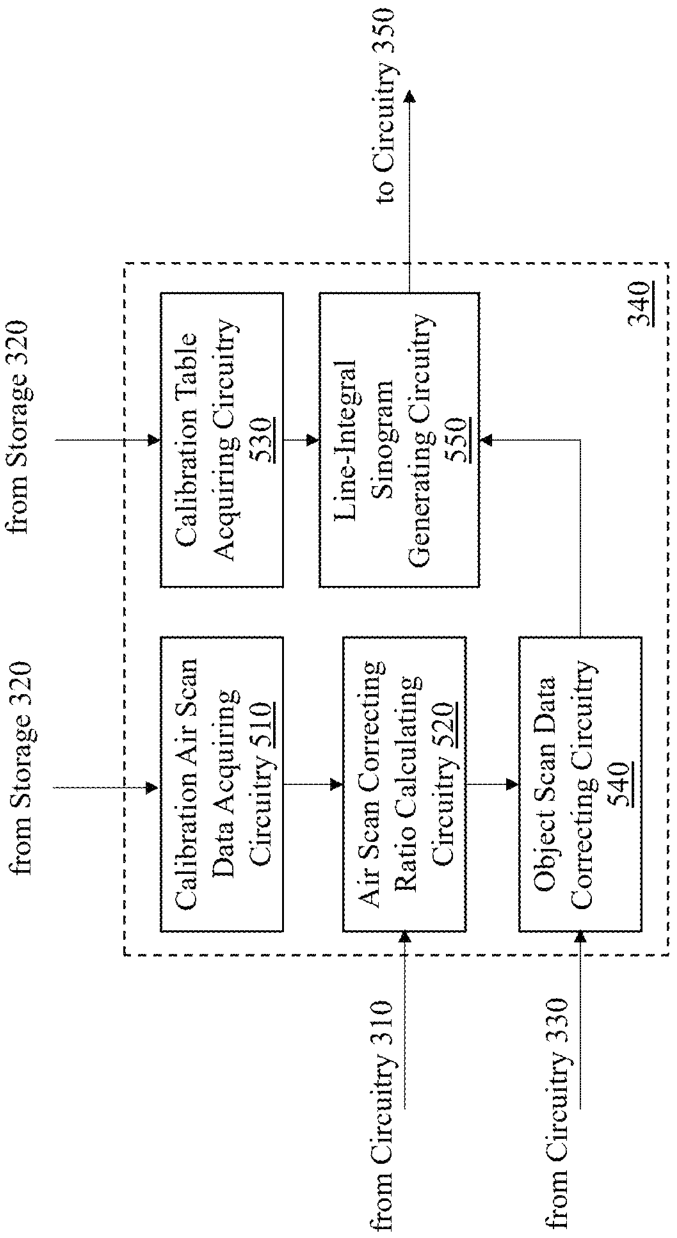
FIG. 5 shows a block diagram of detector response correction circuitry 340 according to embodiments of the disclosure.

FIG. 5 shows a block diagram of the detector response correction circuitry 340 according to embodiments of the disclosure. The detector response correction circuitry 340 includes calibration air scan data acquiring circuitry 510, air scan correcting ratio calculating circuitry 520, calibration table acquiring circuitry 530, object scan data correcting circuitry 540, and line-integral sinogram generating circuitry 550.

The calibration air scan data acquiring circuitry 510 retrieves, from the calibration data storage 320, the scan data generated during the calibration air scan, and sends it to the air scan correcting ratio calculating circuitry 520. The air scan correcting ratio calculating circuitry 520 also receives the most recent air scan data from the air scan data acquiring circuitry 310. Based on these original and new air scan data, the air scan correcting ratio calculating circuitry 520 calculates air scan correcting ratios in a pixel-by-pixel, energy-bin-by-energy-bin manner.

In order to isolate other system-related variations, static scan conditions are used for air scans, which means during the scan the gantry remains stationary. For example, air scans can be routinely executed or initiated upon meeting certain criteria, using identical scan conditions as those used during the calibration air scan. This ensures that the detector response drift can be accurately captured.

For a pixel j and an energy bin b, let $N_{air}$(j, b) denote the count per integration time measured originally during the calibration air scan, and $N_{air}'$(j, b) denote the count measured during a subsequent air scan. Assuming that the detector response drift does not have any spectrum or flux dependency, an air scan correcting ratio for that specific pixel and energy bin can be calculated as follows:

$$R_{air}(j, b) = N'_{air}(j, b)/N_{air}(j, b) \tag{4}$$

The object scan data correcting circuitry 540 receives the calculated air scan correcting ratios from the air scan correcting ratio calculating circuitry 520, along with the object scan data from the object scan data acquiring circuitry 330. Based on the air scan correcting ratios received, the object scan data correcting circuitry 540 can modify or correct the object scan data.

In this disclosure, the object scan data is always collected after both the calibration air scan and the latest air scan. Let $$N'_{obj}(j, b, k)$$

denote the count per integration time measured during the object scan for the pixel j and the energy bin b, with k representing the scan view index. The corresponding air scan correcting ratio $R_{air}$(j, b) can be applied to the object scan data $N'_{air}$(j, b, k) as follows:

$$N_{obj}(j, b, k) = N'_{obj}(j, b, k)/R_{air}(j, b) \tag{5}$$

By implementing this correction process, the adjusted measurement $N_{obj}$(j, b, k) is derived, with the detector response corrected as if it remains its original state at the time of the full calibration.

The calibration table acquiring circuitry 530 retrieves a calibration table from the calibration data storage 320, and sends it to the line-integral sinogram generating circuitry 550. In addition to the calibration table, the line-integral sinogram generating circuitry 550 receives the adjusted object scan data from the object scan data correcting circuitry 540. Based on the calibration table, the line-integral sinogram generating circuitry 550 uses the adjusted object scan data to generate a line-integral sinogram, which is sent to the object image reconstruction circuitry 350 for image reconstruction.

Figure 6:
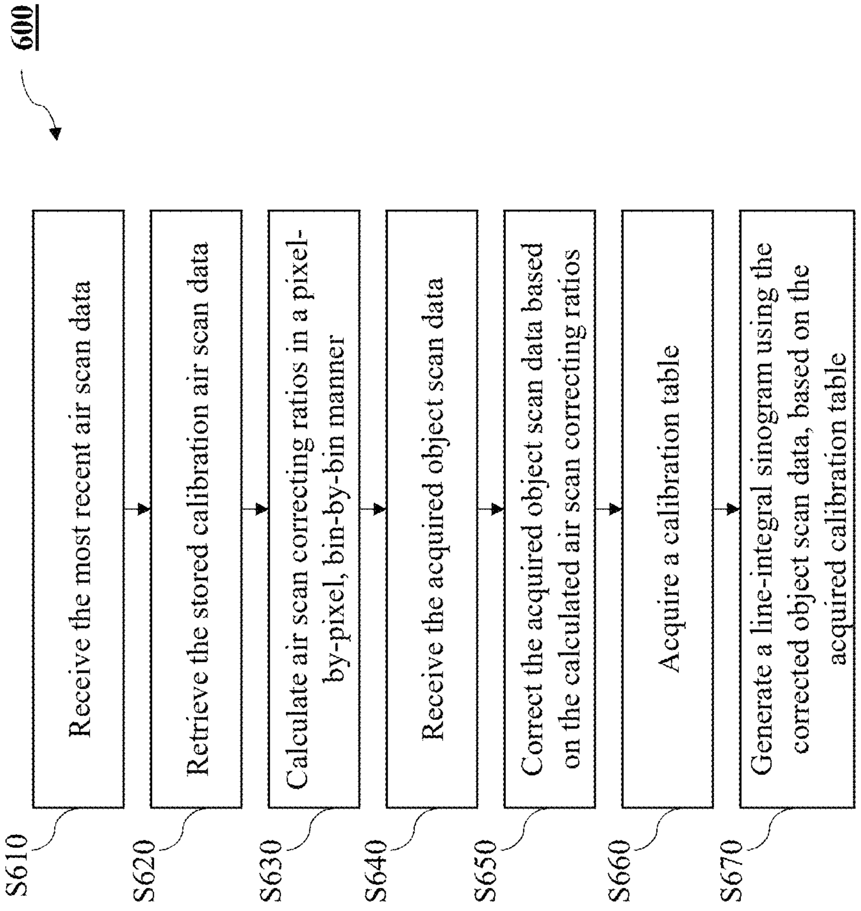
FIG. 6 shows a flow chart of a detector response correction procedure 600 according to embodiments of the disclosure.

FIG. 6 shows a flow chart of a detector response correction procedure 600 according to embodiments of the disclosure. In step S610, scan data acquired through the most recent air scan is received. In step S620, scan data generated from the air scan performed during the full calibration is retrieved. In step S630, air scan correcting ratios are calculated in a pixel-by-pixel, energy-bin-by-energy-bin manner, based on the received air scan data and the retrieved calibration air scan data. In step S640, the object scan data generated from the object scan is received. In step S650, the received object scan data is corrected based on the calculated air scan correcting ratios. In step S660, a calibration table is acquired. In step S670, a line-integral sinogram is generated using the corrected object scan data, based on the acquired calibration table.

In the embodiment shown in FIGS. 5-6, the air scan correcting ratios are used to adjust the object scan data, as if the detector response remains as it were at the time of the full calibration. Alternatively, calibration tables can be modified based on the air scan correcting ratios. For example, the air scan correcting ratios can be used to adjust the slab scan data, simulating slab calibration data generated with the current detector response, thereby generating a new set of detector response calibration tables. These new calibration tables can be used in the generation of line integral sinograms, instead of the initial calibration tables prepared during the full calibration.

Figure 7:
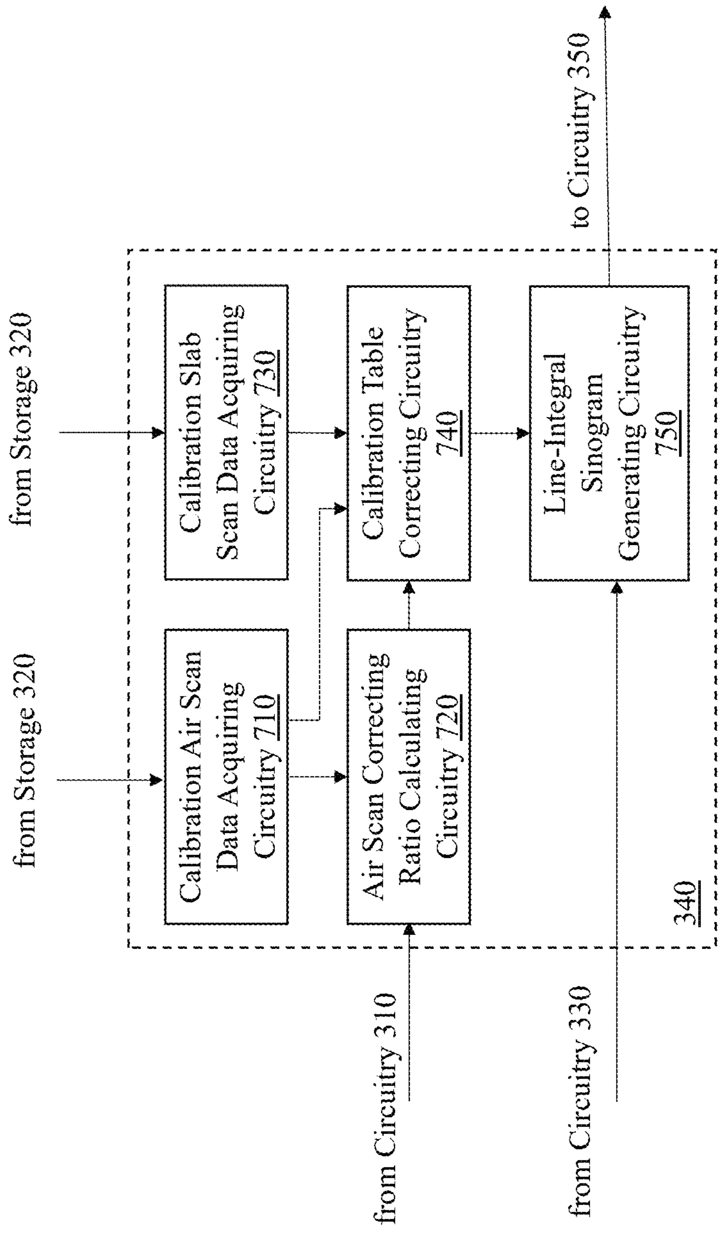
FIG. 7 shows a block diagram of detector response correction circuitry 340 according to embodiments of the disclosure.

FIG. 7 shows a block diagram of detector response correction circuitry 340 according to embodiments of the disclosure. The detector response correction circuitry 340 includes calibration air scan data acquiring circuitry 710, air scan correcting ratio calculating circuitry 720, calibration slab scan data acquiring circuitry 730, calibration table correcting circuitry 740, and line-integral sinogram generating circuitry 750. The functions of the calibration air scan data acquiring circuitry 710 and the air scan correcting ratio calculating circuitry 720 are identical to those of the corresponding components of the detector response correction circuitry 340 of FIG. 3.

As previously discussed, instead of using the air scan correcting ratios to refine the object scan data, detector response correction can be achieved by calibration table correction. The calibration slab scan data acquiring circuitry 730 retrieve calibration slab scan data from the calibration data storage 320, and sends it to the calibration table correcting circuitry 740. In addition to the calibration slab scan data, the calibration table correcting circuitry 740 receives the calibration air scan data from the calibration air scan data acquiring circuitry 710 and the air scan correcting ratios from the air scan correcting ratio calculating circuitry 720. Based on the air scan correcting ratios, the calibration table correcting circuitry 740 can adjust the received calibration slab scan data, and generate a set of corrected calibration tables based on the adjusted calibration slab scan data and the received calibration air scan data.

Then, the line-integral sinogram generating circuitry 750 obtains an adjusted calibration table from the calibration table correcting circuitry 740. Based on the adjusted calibration table, the line-integral sinogram generating circuitry 750 uses the object scan data received from the object scan data acquiring circuitry 330 to generate a line-integral sinogram, which is sent to the object image reconstruction circuitry 350 for image reconstruction.

For example, considering the pixel j and energy bin b, the air scan correcting ratio $R_{air}(j, b)$ can be applied to calibration slab scan data $N_{slab}(i, j, b)$, deriving the adjusted calibration slab scan data $N'_{slab}(i, j, b)$ as follows:

$$N'_{slab}(i, j, b) = N_{slab}(i, j, b) * R_{air}(j, b) \quad (6)$$

Therefore, in this embodiment, a new set of calibration tables for the forward model are generated based on the adjusted calibration slab scan data, while the object scan data remains unchanged.

Figure 8:
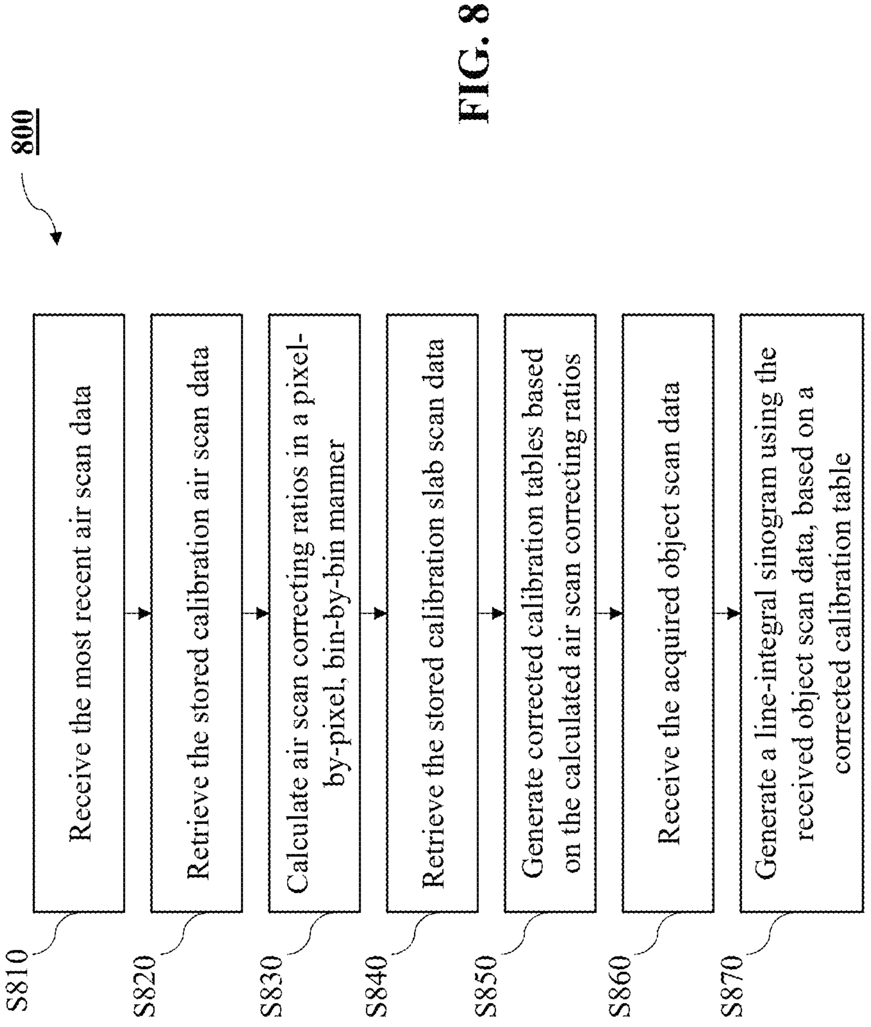
FIG. 8 shows a flow chart of a detector response correction procedure 800 according to embodiments of the disclosure.

FIG. 8 shows a flow chart of a detector response correction procedure 800 according to embodiments of the disclosure. In step S810, the most recent air scan data is received. In step S820, the stored calibration air scan data is retrieved. In step S830, air scan correcting ratios are calculated in a pixel-by-pixel, energy-bin-by-energy-bin manner, using the received air scan data and the retrieved calibration air scan data. In step S840, the stored calibration slab scan data is acquired. In step S850, corrected calibration tables are generated based on the air scan correcting ratios. In step S860, the acquired object scan data is received. In step S870, a line-integral sinogram is generated using the acquired object scan data, based on a corrected calibration table.

The embodiments depicted in FIGS. 5-6 and 7-8 can maintain a consistent detector response, thereby facilitating the generation of corrected object scan line integrals and the reconstruction of high-quality object images. However, neither approach considers the spectrum differences between an air scan and a scan subjected to attenuation. In contrast, an alternative approach that takes into account such spectrum differences is described with reference to FIGS. 9A-9B and 10-12.

Figure 9A:
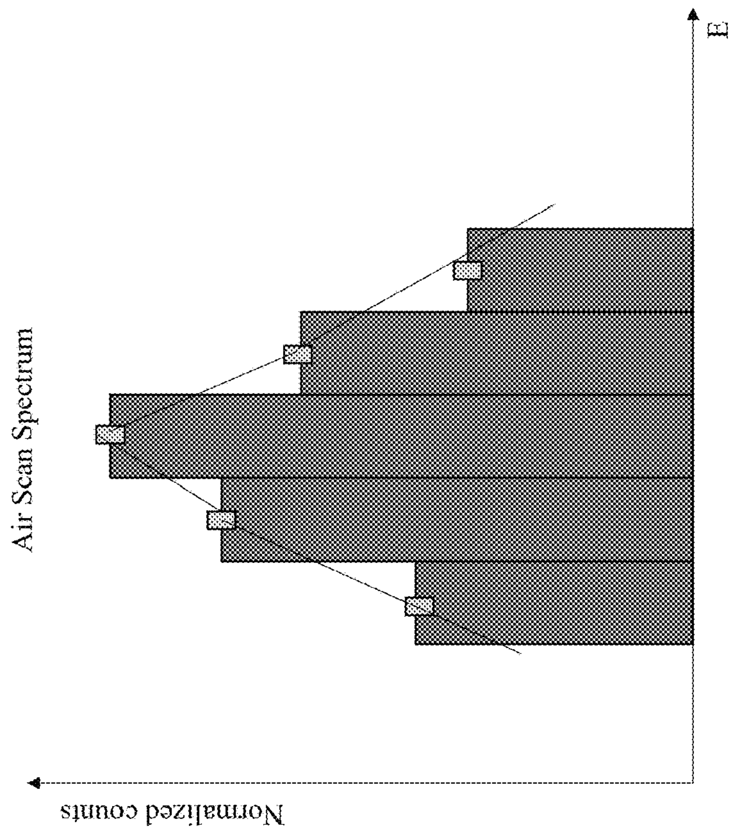
FIGS. 9A-9B show exemplary normalized spectrums of an air scan and an attenuation scan according to embodiments of the disclosure.
Figure 9B:
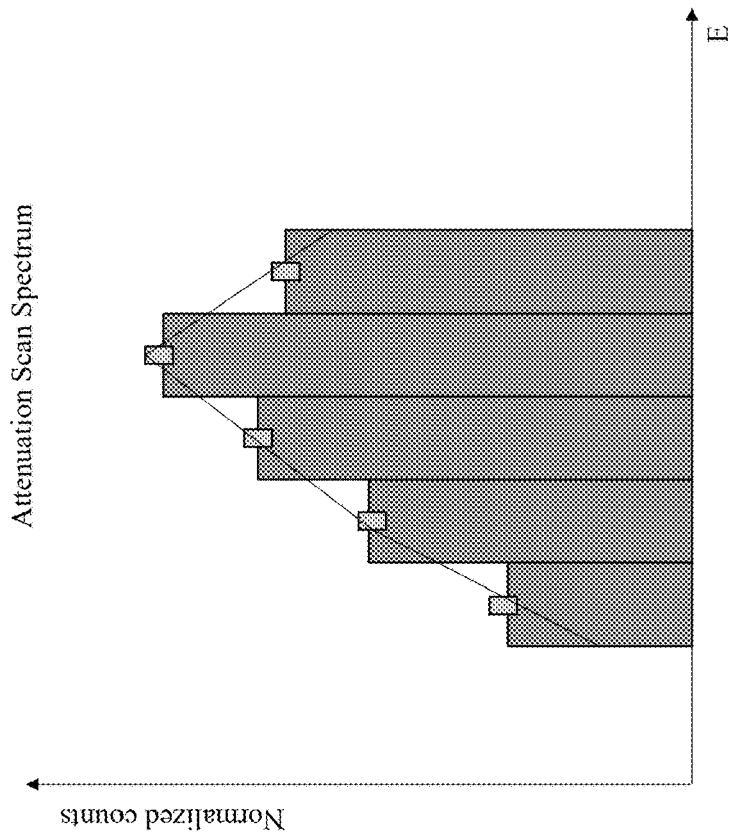

FIGS. 9A-9B show exemplary normalized spectrums of an air scan and an attenuation scan according to embodiments of the disclosure. As can be seen from the figures, a major difference is that with attenuation, the measured spectrum becomes harder, resulting in an increase in high energy bin counts compared to low energy bin counts.

To account for the spectrum dependency in the detector response drift, a weighting mechanism can be applied to address the spectrum differences between air and attenuation scans, for example. This approach can include estimating attenuation scan correcting ratios based on the calculated air scan correcting ratios $R_{air}(j, b)$. By doing so, a more accurate correction can be achieved compared with directly applying $R_{air}(j, b)$ to the object scan data (or the calibration slab scan data).

More specifically, the data acquired from a slab scan during the full calibration procedure can be used to calculate slab scan correcting ratios, based on the air scan correcting ratios $R_{air}(j, b)$. When used in the detect response correction for the object scan, these slab scan correcting ratios, denoted as $R_{slab}(j, b)$, can provide a reliable approximation of the attenuation scan correcting ratios. Given that the attenuation scan spectrum is largely stable for most detector pixels, this approximation is generally valid.

Figure 10:
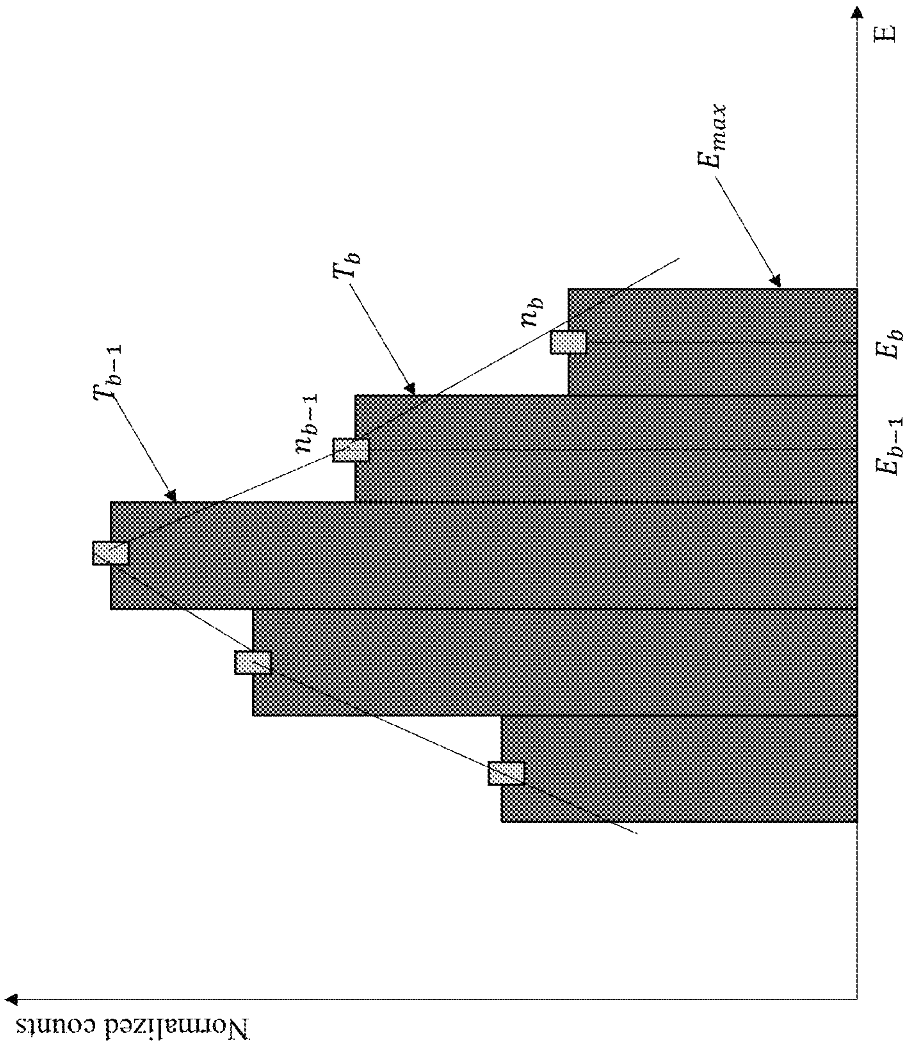
FIG. 10 shows a scenario where an effective energy threshold drift is calculated based on the normalized air scan spectrum shown in FIG. 9A.

FIG. 10 shows exemplary calculation of an effective energy threshold drift using the normalized air scan spectrum depicted in FIG. 9A. In this scenario, a linear interpolation method is applied to the measured bin counts of two neighboring energy bins to obtain an approximation of the measured spectrum, as shown in FIG. 10. When the effective energy threshold drifts, a correcting ratio for a spectrum subjected to attenuation can be estimated based on a corresponding air scan correcting ratio.

As exemplarily shown in FIG. 10, for a given pixel, the measurement in the highest energy bin b counts the photons with energy greater than $T_b$. If the air scan correcting ratio $R_{air}(b)$ calculated for this energy bin is less than 1 ($R_{air}(b) < 1$), it indicates that the most recent air scan has more counts in this energy bin, likely due to the corresponding energy threshold $T_b$ being lower than before. Let $E_b$ denote the center energy of the energy bin b, and $E_{b-1}$ denote the center energy of the energy bin b−1. An air spectrum slope $S_b$(air) around this energy region can be calculated using the calibration air scan data as follows:

$$S_b(\text{air}) = (n_b(\text{air}) - n_{b-1}(\text{air}))/(E_b - E_{b-1}) \tag{7}$$

where $n_b$(air) and $n_{b-1}$(air) are energy bin width normalized counts, $N_b$(air) and $N_{b-1}$(air) are the counts measured within the two energy bins b and b−1 during the calibration air scan, $$n_b(\text{air}) = \frac{N_b(\text{air})}{W_b},$$

$$n_{b-1}(\text{air}) = \frac{N_{b-1}(\text{air})}{W_{b-1}},$$

$$W_b = Emax - T_b, \text{ and}$$

$$W_{b-1} = T_b - T_{b-1}.$$

Furthermore, using the air scan correcting ratio $R_{air}(b)$, an air scan normalized count drift $\delta n_b$ can be calculated for the energy bin b, as follows:

$$\delta n_b(\text{air}) = (R_{air}(b) - 1) * N_b(\text{air})/W_b \tag{8}$$

Then, based on the calculation from Equations (7) and (8), an effective energy threshold drift $\delta T_b$ of the energy bin b can be derived as follows:

$$\delta T_b = \delta n_b(\text{air})/S_b(\text{air}) \tag{9}$$

In a manner similar to the calculation of $S_b$(air), an attenuation spectrum slope $S_b$(slab) in this energy region can be calculated as follows, using the scan data generated through a slab scan during the calibration procedure:

$$S_b(\text{slab}) = (n_b(\text{slab}) - n_{b-1}(\text{slab}))/(E_b - E_{b-1}) \tag{10}$$

where $n_b$(slab) and $n_{b-1}$(slab) are energy bin width normalized counts, $N_b$(slab) and $N_{b-1}$(slab) are the counts measured for the two energy bins b and b−1 during the calibration slab scan, $$n_b(\text{slab}) = \frac{N_b(\text{slab})}{W_b}, \text{ and}$$

$$n_{b-1}(\text{slab}) = \frac{N_{b-1}(\text{slab})}{W_{b-1}}.$$

From the effective energy threshold drift $\delta T_b$ calculated with Equation (9) and the attenuation spectrum slope $S_b$(slab) calculated with Equation (10), an attenuation scan count drift $\delta N_b$(slab) can be derived as follows:

$$\delta N_b(\text{slab}) = S_b(\text{slab}) * \delta T_b * W_b \tag{11}$$

Then, an attenuation scan correcting ratio $R_{slab}(b)$ that considers the spectrum differences between the air and attenuation scans can be calculated as:

$$R_{slab}(b) = 1 + \delta N_b(\text{slab}) * N_b(\text{slab}) \tag{12}$$

Once the attenuation scan correcting ratio is calculated for the specific pixel and the specific energy bin, it can replace the corresponding air scan correcting ratio to be applied in the above Equation (5) or (6) for implementing the detector response correction.

Similar calculations can be performed for lower energy bin thresholds, e.g., $T_{b-1}$, after considering the estimated higher threshold drift for the selected energy bin measurement. For instance, the following calculations (13)-(17) can be performed:

$$S_{b-1}(\text{air}) = (n_{b-1}(\text{air}) - n_{b-2}(\text{air}))/(E_{b-1} - E_{b-2}) \tag{13}$$

$$\delta n_{b-1}(\text{air}) = (R_{air}(b-1) - 1) * N_{b-1}(\text{air})/W_{b-1} \tag{14}$$

$$\delta T_{b-1} = (\delta n_{b-1}(\text{air}) + \delta n_b(\text{air}))/S_{b-1}(\text{air}) \tag{15}$$

$$\delta N_{b-1}(\text{slab}) = S_{b-1}(\text{slab}) * \delta T_{b-1} * W_{b-1} \tag{16}$$

$$R_{slab}(b-1) = 1 + \delta N_{b-1}(\text{slab}) * N_{b-1}(\text{slab}) \tag{17}$$

In the previous description, linear interpolation of the measured spectrum is used. Alternatively, higher order polynomials and additional constraints involving more than two adjacent bin counts can be used to fit the function parameters. In such cases, the slope $S_b$ can be replaced by the first derivative of the polynomial functions at the corresponding energy threshold, for example.

Figure 11:
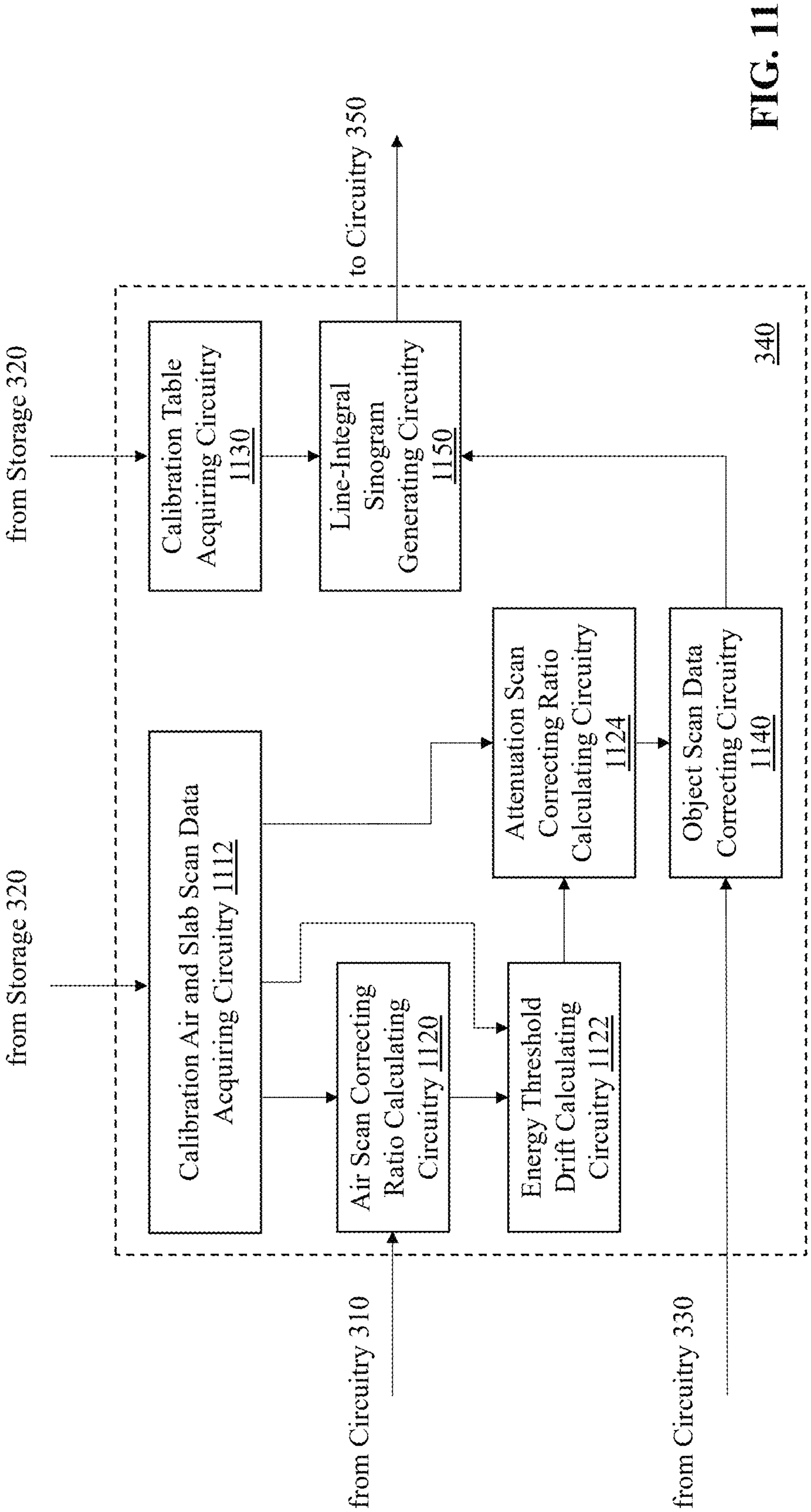
FIG. 11 shows a block diagram of detector response correction circuitry 340 according to embodiments of the disclosure.

FIG. 11 shows a block diagram of detector response correction circuitry 340 according to embodiments of the disclosure. The detector response correction circuitry 340 includes calibration air and slab scan data acquiring circuitry 1112, air scan correcting ratio calculating circuitry 1120, energy threshold drift calculating circuitry 1122, attenuation scan correcting ratio calculating circuitry 1124, calibration table acquiring circuitry 1130, object scan data correcting circuitry 1140, and line-integral sinogram generating circuitry 1150.

The calibration air and slab scan data acquiring circuitry 1112 acquires calibration air scan data and calibration slab scan data from the calibration data storage 320. The air scan correcting ratio calculating circuitry 1120 receives the calibration air scan data from the calibration air and slab scan data acquiring circuitry 1112 and the most recent air scan data from the air scan data acquiring circuitry 310. Based on both sets of data, the air scan correcting ratio calculating circuitry 1120 calculates air scan correcting ratios in a pixel-by-pixel, energy-bin-by-energy-bin manner.

The energy threshold drift calculating circuitry 1122 receives the air scan correcting ratios calculated by the air scan correcting ratio calculating circuitry 1120, and the calibration air scan data from the calibration air and slab scan data acquiring circuitry 1112. Based on the air scan correcting ratios and the calibration air scan data, the energy threshold drift calculating circuitry 1122 calculates energy threshold drifts, and sends them to the attenuation scan correcting ratio calculating circuitry 1124.

The attenuation scan correcting ratio calculating circuitry 1124 calculates a corresponding attenuation scan correcting ratio for each air scan correcting ratio, based on the energy threshold drifts received from the energy threshold drift calculating circuitry 1122 and calibration slab scan data received from the calibration air and slab scan data acquiring circuitry 1112.

The object scan data correcting circuitry 1140 receives the object scan data from the object scan data acquiring circuitry 330 and the attenuation scan correcting ratios from the attenuation scan correcting ratio calculating circuitry 1124, and adjusts the object scan data based on the attenuation scan correcting ratios.

The calibration table acquiring circuitry 1130 acquires a calibration table from the calibration data storage 320, and sends it to the line-integral sinogram generating circuitry 1150. In addition to the calibration table, the line-integral sinogram generating circuitry 1150 receives the adjusted object scan data from the object scan data correcting circuitry 1140. Based on the calibration table, the line-integral sinogram generating circuitry 1150 uses the adjusted object scan data to generate a line-integral sinogram, which is then sent to the object image reconstruction circuitry 350 for image reconstruction.

Figure 12:
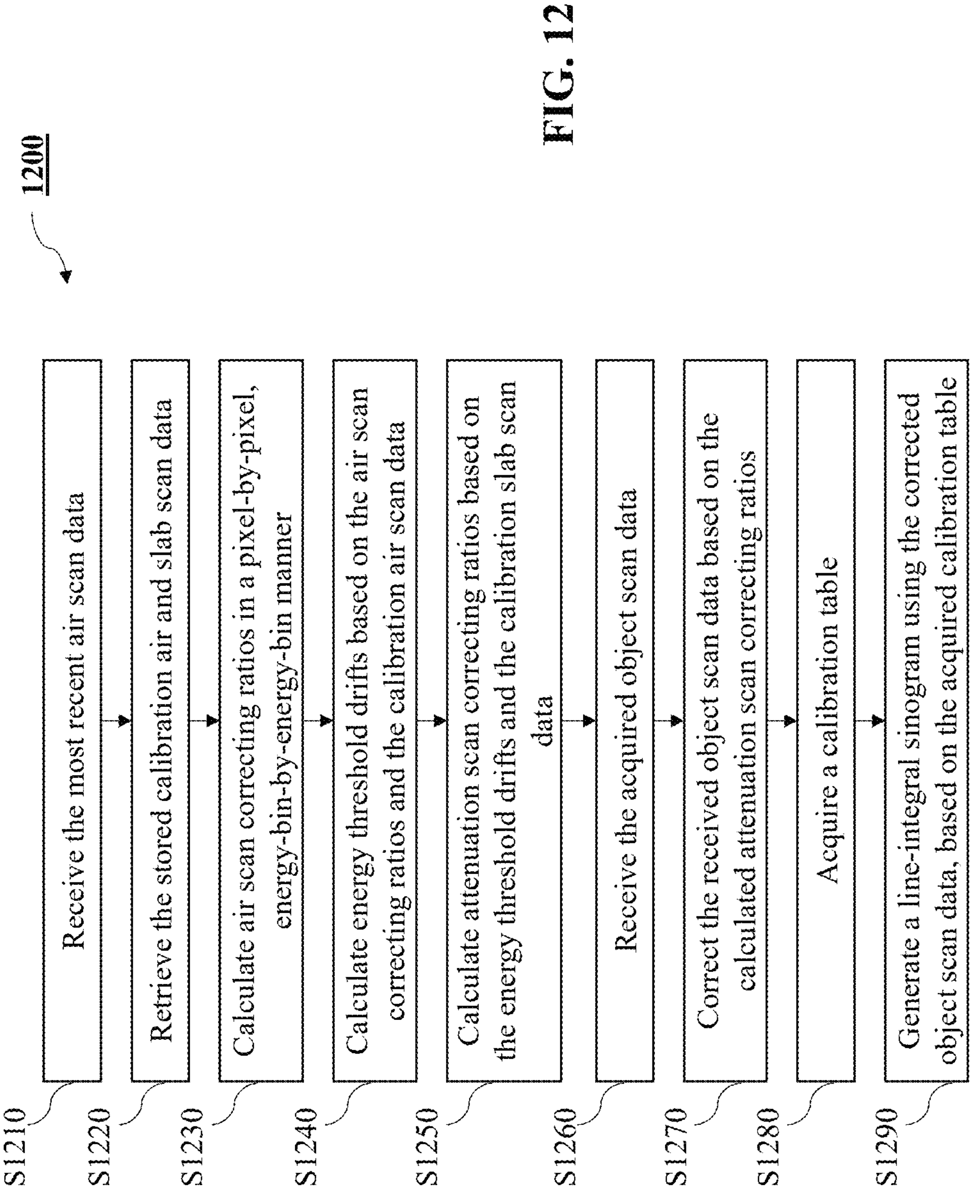
FIG. 12 shows a flow chart of a detector response correction procedure 1200 according to embodiments of the disclosure.

FIG. 12 shows a flow chart of a detector response correction procedure 1200 according to embodiments of the disclosure. In step S1210, the most recent air scan data is received. In step S1220, the stored calibration air and slab scan data is retrieved. In step S1230, air scan correcting ratios are calculated pixel by pixel, energy bin by energy bin, based on the most recent air scan data and the calibration air scan data.

In step S1240, energy threshold drifts are calculated based on the air scan correcting ratios and the calibration air scan data. In step S1250, attenuation scan correcting ratios are calculated based on the energy threshold drifts and the calibration slab scan data. In step S1260, the acquired object scan data is received. In step S1270, the received object scan data is corrected based on the calculated attenuation scan correcting ratios. In step S1280, a calibration table is acquired. In step S1290, a line-integral sinogram is generated using the corrected object scan data, based on the calibration table.

Similarly to the embodiment of FIGS. 7-8, in this embodiment, the detector response correction can be implemented by modifying the calibration tables instead of the object scan data. That is, the object scan data can remain untouched, while the calibration slab scan data can be adjusted based on the attenuation scan correcting ratios. Then, new calibration tables for the forward model can be generated based on the adjusted calibration slab scan data, and be used in the generation of line-integral sinograms.

As mentioned earlier, correcting ratios calculated using the calibration slab scan data are used during the detector response correction of the object scan, so as to account for the spectrum differences between air and attenuation scans. Depending on an estimated attenuation pathlength of the object scan, scan data acquired using a slab with the closest pathlength can be selected to calculate the slab scan correcting ratios. For example, for each view of the object scan data, among the slab scan data previously collected using a plurality of slabs during the full calibration, the data obtained from a slab that has the closest pathlength to the attenuation pathlength of the view can be selected.

Furthermore, to reduce the flux dependency in the calculation of the slab scan correcting ratios, a proper tube current can be selected for the air scans, such that the count rates caused matches that of the slab scan. By doing so, the accuracy of the detector response correction can be enhanced, and the flux dependency due to pileup effects can be suppressed.

In addition, as the object scan can be performed with various tube currents, the above-discussed correcting ratio calculations can be conducted for slab scans performed under a plurality of different tube currents. When the correcting ratios are calculated from a slab scan with a tube current similar to that used in the object scam, the correction accuracy can be further increased.

This disclosure relates to detector response corrections used in a photon-counting CT scanner system, said CT scanner system comprising one or more X-ray tubes that emit X-ray radiation, and an array of detector pixels for receiving the X-ray radiation propagating through a field of view (FOV) of the CT scanning system. The detector response correction scheme can be applied to both the PCD counting and the spectral forward models.

Figure 13:
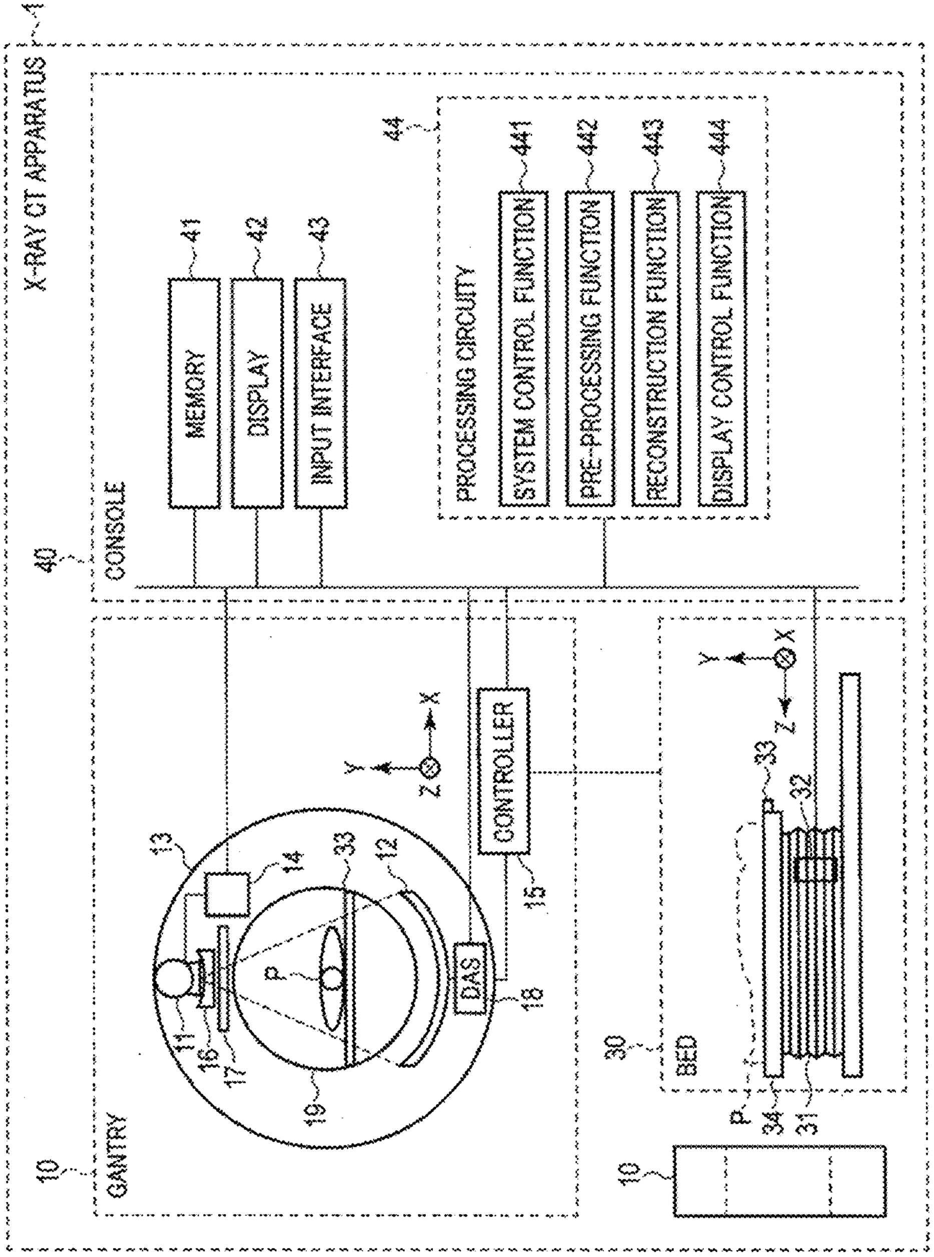
FIG. 13 shows an example of a photon-counting Computed Tomography scanner system that can incorporate the techniques disclosed herein.

The detector response correcting approach can be implemented in a photon-counting CT scanning system as described below with reference to FIG. 13. The X-ray CT apparatus 1 shown in FIG. 13 includes a gantry 10, a bed 30, and a console 40 that implements the processing of the medical imaging processing apparatus. For the sake of explanation, FIG. 13 shows multiple gantries 10.

In the present embodiment, the rotation axis of a rotation frame 13 in the non-tilted state, or the longitudinal direction of a table top 33 of the bed 30, is defined as a "Z-axis direction;" the axial direction orthogonal to the Z-axis direction and horizontal to the floor is defined as an "X-axis direction;" and the axial direction orthogonal to the Z-axis direction and vertical to the floor is defined as a "Y-axis direction."

For example, the gantry 10 and the bed 30 are installed in a CT examination room, and the console 40 is installed in a control room adjacent to the CT examination room. The console 40 is not necessarily installed in the control room. For example, the console 40 can be installed together with the gantry 10 and the bed 30 in the same room. In any case, the gantry 10, the bed 30, and the console 40 are communicably connected to one another by wire or radio.

The gantry 10 is a scanner with a configuration for performing X-ray CT imaging on a subject (or an imaging object) P. The gantry 10 includes an X-ray tube 11, an X-ray detector 12, a rotation frame 13, an X-ray high voltage device 14, a controller 15, a wedge filter 16, a collimator 17, and a data acquisition system (DAS) 18.

The X-ray tube 11 is a vacuum tube that generates X-rays by emitting thermal electrons from the cathode (filament) to the anode (target) in response to application of a high voltage and supply of a filament current from the X-ray high voltage device 14. Specifically, X-rays are generated by the thermal electrons colliding with the target. Examples of the X-ray tube 11 include a rotating anode type X-ray tube that generates X-rays by emitting thermal electrons to the rotating anode. The X-rays generated in the X-ray tube 11 are, for example, formed into a cone-beam shape by the collimator 17, and applied to the subject P.

The X-ray detector 12 detects X-rays that have been emitted by the X-ray tube 11 and have passed through the subject P, and outputs an electrical signal corresponding to the X-ray dose to the DAS 18. The X-ray detector 12 includes a plurality of X-ray detection element lines, each including a plurality of X-ray detection elements aligned in the channel direction (the X-axis direction, or the column direction) along an arc having a center at the focus of the X-ray tube 11, for example. The X-ray detector 12 has an array structure in which a plurality of X-ray detection element lines, each including a plurality of X-ray detection elements aligned in the channel direction, are aligned in the segment direction (the Z-axis direction, or the row direction).

Specifically, the X-ray detector 12 can be, for example, a direct conversion type detector including a semiconductor element that converts incident X-rays into an electrical signal. The X-ray detector 12 is an example of the PCD according to the present embodiment, and will also be referred to as a "PCD 12."

The rotation frame 13 supports an X-ray generator and the X-ray detector 12 rotatably around a rotation axis. Specifically, the rotation frame 13 is an annular frame that supports the X-ray tube 11 and the X-ray detector 12 in such a manner that the X-ray tube 11 faces the X-ray detector 12, and rotates the X-ray tube 11 and the X-ray detector 12 under the control of a controller 15 to be described later. The rotation frame 13 is rotatably supported by a stationary frame (not shown) made of a metal such as aluminum. Specifically, the rotation frame 13 is connected to an edge portion of the stationary frame via a bearing. The rotation frame 13 rotates around the rotation axis Z at a predetermined angular velocity while receiving power from a driver of the controller 15.

In addition to the X-ray tube 11 and the X-ray detector 12, the rotation frame 13 includes and supports the X-ray high voltage device 14 and the DAS 18. Such a rotation frame 13 is housed in an approximately-cylindrical case with a bore 19 constituting an imaging space. The bore approximately corresponds to the FOV. The central axis of the bore corresponds to the rotation axis Z of the rotation frame 13. Detection data generated by the DAS 18 is transmitted, for example, from a transmitter (not shown) to a receiver (not shown) arranged on a non-rotating portion (such as the stationary frame, illustration omitted in FIG. 13) of the gantry, and then transferred to the console 40.

The X-ray high voltage device 14 includes: a high voltage generator including electrical circuitry such as a transformer, a rectifier, etc. and having the function of generating a high voltage to be applied to the X-ray tube 11 and a filament current to be supplied to the X-ray tube 11; and an X-ray controller configured to control an output voltage in accordance with the X-rays emitted by the X-ray tube 11. The high voltage generator can be of a transformer type, or an inverter type. The X-ray high voltage device 14 may be provided in the rotation frame 13 to be described later, or in the stationary frame (not shown) of the gantry 10.

The controller 15 includes processing circuitry including a central processing unit (CPU), etc., and a driver such as a motor or an actuator, etc. The processing circuitry includes, as hardware resources, a processor, such as a CPU or a micro processing unit (MPU), and a memory, such as a read only memory (ROM) or a random access memory (RAM). The controller 15 can be realized by an application specific integrated circuit (ASIC), a field programmable gate array (FPGA), or another complex programmable logic device (CPLD) or simple programmable logic device (SPLD). The controller 15 controls the X-ray high voltage device 14 and the DAS 18, etc. in accordance with instructions from the console 40. The processor implements the above control by reading and executing a program stored in the memory.

The CPU can execute a computer program including a set of computer-readable instructions that perform the functions described herein, and the program is stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor and an operating system known to those skilled in the art. Further, the CPU can be implemented as multiple processors cooperatively working in parallel to perform the instructions.

The controller 15 also has the function of performing operation control of the gantry 10 and the bed 30 in response to an input signal from an input interface 43 to be described later attached to the console 40 or the gantry 10. For example, the controller 15 performs control to rotate the rotation frame 13, control to tilt the gantry 10, or control to operate the bed 30 and the table top 33 in response to an input signal. The control to tilt the gantry 10 is implemented by the controller 15 rotating the rotation frame 13 around an axis parallel to the X-axis direction, based on tilt angle information input through the input interface 43 attached to the gantry 10. The controller 15 may be provided either in the gantry 10 or in the console 40. The controller 15 may be configured by directly integrating a program in the circuitry of the processor, instead of storing a program in the memory. In this case, the processor implements the above-described control by reading and executing the program integrated in the circuitry.

The wedge filter 16 is a filter for adjusting the dose of X-rays emitted from the X-ray tube 11. Specifically, the wedge filter 16 is a filter that allows X-rays emitted from the X-ray tube 11 to pass therethrough, and attenuates the X-rays so that the X-rays emitted from the X-ray tube 11 to the subject P exhibit predetermined distribution. For example, the wedge filter 16 (or bow-tie filter) is a filter obtained by processing aluminum so that it has a predetermined target angle and a predetermined thickness.

The collimator 17 is lead plates or the like for narrowing the application range of X-rays that have passed through the wedge filter 16, and includes a slit formed by combining the lead plates or the like. The collimator 17 may be referred to as an "X-ray diaphragm."

The DAS 18 generates digital data indicating counts of X-rays detected by the X-ray detector 12 (also referred to as "detection data") for each of a plurality of energy bands (referred to as "energy bins" or simply as "bins"). The detection data is a set of a channel number and row number of a source X-ray detection element, a view number indicating a collected view (also referred to as a projection angle), and data of the count value identified by the energy bin number. The DAS 18 is implemented by, for example, an application specific integrated circuit (ASIC) on which a circuit element capable of generating detection data is mounted. The detection data is transferred to the console 40.

The bed 30 is a device to place thereon the subject P to be scanned and move the subject P, and includes a base 31, a bed actuator 32, a table top 33, and a support frame 34.

The base 31 is a case that supports the support frame 34 movably in the vertical direction.

The bed actuator 32 is a motor or actuator that moves the table top 33 on which the subject P is placed in the longitudinal direction of the table top 33. The bed actuator 32 moves the table top 33 in accordance with control by the console 40 or control by the controller 15. For example, the bed actuator 32 moves the table top 33 in the direction orthogonal to the subject P so that the body axis of the subject P placed on the table top 33 matches the central axis of the bore of the rotation frame 13. The bed actuator 32 may also move the table top 33 in the body axis direction of the subject P in accordance with X-ray CT imaging performed using the gantry 10. The bed actuator 32 generates power by driving at a rotation speed corresponding to the duty ratio of the drive signal from the controller 15. The bed actuator 32 is implemented by a motor, such as a direct drive motor or a servo motor.

The table top 33 provided on the top surface of the support frame 34 is a plate on which the subject P is placed. The bed actuator 32 may move not only the table top 33 but the support frame 34 in the longitudinal direction of the table top 33.

The console 40 includes a memory 41, a display 42, an input interface 43, and processing circuitry 44. Data communication between the memory 41, the display 42, the input interface 43, and the processing circuitry 44 is performed via a bus. The console 40 is described as being separate from the gantry 10, but the gantry 10 may include the console 40 or part of each constituent element of the console 40.

The memory 41 is a storage device, such as a hard disk drive (HDD), a solid state drive (SSD), or an integrated circuit storage device, etc., which stores various types of information. The memory 41 stores, for example, projection data and reconstructed image data. The memory 41 may be not only the HDD, SSD, or the like, but a driver that writes and reads various types of information in and from, for example, a portable storage medium such as CD, DVD, or a flash memory, or a semiconductor memory such as a random access memory (RAM). The storage area of the memory 41 may be in the X-ray CT apparatus 1, or in an external storage device connected via the network. For example, the memory 41 stores data of a CT image or a display image. The memory 41 also stores a control program according to the present embodiment.

The display 42 displays various types of information. For example, the display 42 outputs a graphical user interface (GUI) or the like for receiving a medical image (CT image) generated by the processing circuitry 44, and various types of operations from the operator. For the display 42, for example, a liquid crystal display (LCD), a cathode ray tube (CRT) display, an organic electro luminescence display (OELD), a plasma display, or any other display can be used as appropriate. The display 42 may be provided in the gantry 10. The display 42 may either be a desktop type or configured by a tablet device capable of wirelessly communicating with the console 40.

The input interface 43 receives various types of input operations from the operator, converts a received input operation into an electrical signal, and outputs the electrical signal to the processing circuitry 44. For example, the input interface 43 receives, from the operator, a collection condition for collecting projection data, a reconstruction condition for reconstructing a CT image, and an image-processing condition for generating a post-processing image from the CT image, etc. For the input interface 43, for example, a mouse, a keyboard, a trackball, a switch, a button, a joystick, a touch pad, or a touch panel display can be used as appropriate. In the present embodiment, the input interface 43 does not necessarily include a physical operation component such as a mouse, a keyboard, a trackball, a switch, a button, a joystick, a touch pad, or a touch panel display. For example, the input interface 43 also includes electrical signal processing circuitry that receives an electrical signal corresponding to an input operation from an external input device provided separately from the apparatus, and outputs the electrical signal to the processing circuitry 44. The input interface 43 may be provided in the gantry 10. The input interface 43 may be configured by a tablet device capable of wirelessly communicating with the console 40.

The processing circuitry 44 controls the overall operation of the X-ray CT apparatus 1 in accordance with the electrical signal of the input operation output from the input interface 43. For example, the processing circuitry 44 includes, as hardware resources, a processor such as a CPU, an MPU, or a graphics processing unit (GPU), and a memory such as a ROM or a RAM. With a processor that executes a program loaded into the memory, the processing circuitry 44 performs a system control function 441, a pre-processing function 442, a reconstruction function 443, and a display control function 444. Each of the functions (the system control function 441, the pre-processing function 442, the reconstruction function 443, and the display control function 444) is not necessarily implemented by a single processing circuit. Processing circuitry can be configured by combining a plurality of independent processors, and the processors can execute respective programs to implement the functions.

The system control function 441 controls each function of the processing circuitry 44 based on an input operation received from the operator via the input interface 43. Specifically, the system control function 441 reads a control program stored in the memory 41, loads it into a memory in the processing circuitry 44, and controls each part of the X-ray CT apparatus 1 in accordance with the loaded control program. For example, the processing circuitry 44 performs each function of the processing circuitry 44 based on an input operation received from the operator via the input interface 43. For example, the system control function 441 obtains a two-dimensional positioning image of the subject P to determine the scan range, imaging condition, etc. The positioning image can also be referred to as a "scanogram" or "scout image."

The pre-processing function 442 generates data obtained by performing pre-processing on detection data output from the DAS 18, such as logarithmic conversion processing, offset correction processing, processing for sensitivity correction between channels, beam hardening correction, and correction for detector calibrations, detector nonlinearities, polar effects, noise balancing, and material decomposition. Data (detection data) before pre-processing and data after pre-processing can be collectively referred to as "projection data." The pre-processing function 442 is an example of the pre-processor.

The reconstruction function 443 generates CT image data by performing reconstruction processing using a filtered back projection method, a successive approximation reconstruction method, a stochastic image reconstruction method, or the like, on the projection data generated by the pre-processing function 442. The reconstruction function 443 is an example of the reconstruction processor. Image filtering, smoothing, volume rendering, or image differential processing can be applied to the CT image data if required. The display control function 444 converts CT image data generated by the reconstruction function 443 into tomographic image data of a given cross section, or three-dimensional image data by a publicly-known method, based on the input operation received from the operator via the input interface 43. The generation of three-dimensional image data can be performed directly by the reconstruction function 443. The display control function 444 is an example of the display controller.

In one implementation, the X-ray tube 11 is a single source emitting a broad spectrum of X-ray energies, and the PCD 12 can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). As mentioned above, semiconductor-based direct X-ray detectors generally have much faster time response than indirect detectors, such as scintillator detectors. The fast time response of direct detectors enables them to resolve individual X-ray detection events, although at the high X-ray fluxes typical in clinical X-ray applications, some pileup of detection events may occur. The energy of a detected X-ray is proportional to the signal generated by the direct detector, and the detection events can be organized into energy bins yielding spectrally resolved X-ray data for spectral CT.

Numerous modifications and variations of the embodiments presented herein are possible in light of the above teachings. It is therefore to be understood that within the scope of the claims, the application may be practiced otherwise than as specifically described herein. The inventions are not limited to the examples that have just been described; it is in particular possible to combine features of the illustrated examples with one another in variants that have not been illustrated.

Embodiments of the present disclosure may also be as set forth in the following parentheticals.

(1) A method for performing detector response correction in an X-ray imaging system having a photon-counting detector, the method comprising: obtaining calibration data stored in a calibration data storage, where the calibration data is generated during a calibration procedure performed with the X-ray imaging system at a first time; acquiring air scan data generated through an air scan performed with the X-ray imaging system at a second time, where the second time is after the first time; performing, with the X-ray imaging system, an object scan on an imaging object at a third time to generate object scan data, where the third time is after the second time; performing, using the generated object scan data, detector response correction based on the acquired air scan data and the obtained calibration data; and reconstructing, based on the performed detector response correction, an image of the imaging object.

(2) The method of (1), wherein the obtaining step further comprises obtaining calibration air scan data and a calibration table stored in the calibration data storage, wherein the calibration air scan data is generated through a calibration air scan performed during the calibration procedure, the step of performing the detector response correction further comprises: calculating, based on the obtained calibration air scan data and the acquired air scan data, an air scan correcting ratio in a pixel-by-pixel, energy-bin-by-energy-bin manner, for a plurality of pixels and a plurality of energy bins, correcting the generated object scan data based on the calculated air scan correcting ratios, and using the corrected object scan data to generate a line-integral sinogram, based on the obtained calibration table, and the reconstructing step further comprises reconstructing the image of the imaging object, based on the generated line-integral sinogram.

(3) The method of (1), wherein the obtaining step further comprises obtaining calibration air scan data and calibration slab scan data stored in the calibration data storage, wherein the calibration air scan data is generated through a calibration air scan performed during the calibration procedure, and the calibration slab scan data is generated through a calibration slab scan performed during the calibration procedure, the step of performing the detector response correction further comprises: calculating, based on the obtained calibration air scan data and the acquired air scan data, an air scan correcting ratio in a pixel-by-pixel, energy-bin-by-energy-bin manner, for a plurality of pixels and a plurality of energy bins, correcting the obtained calibration slab scan data based on the calculated air scan correcting ratios, generating a calibration table based on the obtained calibration air scan data and the corrected calibration slab scan data, and using the generated object scan data to generate a line-integral sinogram, based on the generated calibration table, and the reconstructing step further comprises reconstructing the image of the imaging object, based on the generated line-integral sinogram.

(4) The method of (1), wherein the obtaining step further comprises obtaining calibration air scan data, calibration slab scan data, and a calibration table stored in the calibration data storage, wherein the calibration air scan data is generated through a calibration air scan performed during the calibration procedure, and the calibration slab scan data is generated through a calibration slab scan performed during the calibration procedure, the step of the performing detector response correction further comprises: calculating, based on the obtained calibration air scan data and the acquired air scan data, an air scan correcting ratio in a pixel-by-pixel, energy-bin-by-energy-bin manner, for a plurality of pixels and a plurality of energy bins, calculating, for each specific air scan correcting ratio of the calculated air scan correcting ratios, a corresponding attenuation scan correcting ratio, based on the specific air scan correcting ratio, the obtained calibration air scan data, and the obtained calibration slab scan data, correcting the generated object scan data based on the calculated attenuation scan correcting ratios, and using the corrected object scan data to generate a line-integral sinogram, based on the obtained calibration table, and the reconstructing step further comprises reconstructing the image of the imaging object, based on the generated line-integral sinogram.

(5) The method of (4), wherein the step of calculating the corresponding attenuation scan correcting ratio further comprises: for each specific air scan correcting ratio of the calculated air scan correcting ratios, calculating an energy bin threshold drift for an energy bin corresponding to the specific air scan correcting ratio, based on a linear interpolation or a higher order polynomial function of the obtained calibration air scan data associated with the energy bin and an adjacent energy bin, and calculating, based on the calculated energy bin threshold drift and the obtained calibration slab scan data, the corresponding attenuation scan correcting ratio.

(6) The method of (4), wherein the obtaining step further comprises: selecting, among respective calibration slab scan data generated through a plurality of calibration slab scans performed on a plurality of slabs that have different attenuation pathlengths, calibration slab scan data generated through a calibration slab scan performed on a specific slab that has an attenuation pathlength closest to an attenuation pathlength of the imaging object, as the obtained calibration slab scan data.

(7) The method of (4), wherein during the calibration air scan, a tube current is applied such that a difference between a detector counting rate caused during the calibration air scan and a detector counting rate of the calibration slab scan is less than or equal to a predefined threshold, and the acquiring step further comprises setting a tube current applied during the air scan, such that a difference between a detector counting rate caused during the air scan and the detector counting rate of the calibration slab scan is less than or equal to the predefined threshold.

(8) The method of (4), wherein the obtain step further comprises: selecting, among respective calibration slab scan data generated through a plurality of calibration slab scans performed on a slab with a plurality of different tube currents applied, calibration slab scan data generated through a calibration slab scan with a specific tube current that is closest to a tube current applied in the object scan, as the obtained calibration slab scan data.

(9) The method of (1), wherein the obtaining step further comprises obtaining calibration air scan data and calibration slab scan data stored in the calibration data storage, wherein the calibration air scan data is generated through a calibration air scan performed during the calibration procedure, and the calibration slab scan data is generated through a calibration slab scan performed during the calibration procedure, the step of performing the detector response correction further comprises: calculating, based on the obtained calibration air scan data and the acquired air scan data, an air scan correcting ratio in a pixel-by-pixel, energy-bin-by-energy-bin manner, for a plurality of pixels and a plurality of energy bins, calculating, for each specific air scan correcting ratio of the calculated air scan correcting ratios, a corresponding attenuation scan correcting ratio, based on the specific air scan correcting ratio, the obtained calibration air scan data, and the obtained calibration slab scan data, correcting the obtained calibration slab scan data based on the calculated air scan correcting ratios, generating a calibration table based on the obtained calibration air scan data and the corrected calibration slab scan data, and using the generated object scan data to generate a line-integral sinogram, based on the generated calibration table, and the reconstructing step further comprises reconstructing the image of the imaging object, based on the generated line-integral sinogram.

(10) The method of (1), wherein the acquiring step further comprises acquiring the air scan data generated through the air scan that is performed upon a predefined criterion being met, and the predefined criterion is met when a predefined time period has elapsed since the calibration procedure, when a difference between a condition under which the X-ray imaging system operates and the condition under which the calibration procedure is performed is larger than or equal to a predetermined threshold, and/or when a scan protocol to be applied with the X-ray imaging system is different from a scan protocol that is applied when the calibration procedure is performed.

(11) An apparatus for performing detector response correction in an X-ray imaging system having a photon-counting detector, the apparatus comprising: processing circuitry configured to obtain calibration data stored in a calibration data storage, where the calibration data is generated during a calibration procedure performed with the X-ray imaging system at a first time, acquire air scan data generated through an air scan performed with the X-ray imaging system at a second time, where the second time is after the first time, perform, with the X-ray imaging system, an object scan on an imaging object at a third time to generate object scan data, where the third time is after the second time, perform, using the generated object scan data, detector response correction based on the acquired air scan data and the obtained calibration data, and reconstruct, based on the performed detector response correction, an image of the imaging object.

(12) The apparatus of (11), wherein the processing circuitry is further configured to: obtain calibration air scan data and a calibration table stored in the calibration data storage, wherein the calibration air scan data is generated through a calibration air scan performed during the calibration procedure, calculate, based on the obtained calibration air scan data and the acquired air scan data, an air scan correcting ratio in a pixel-by-pixel, energy-bin-by-energy-bin manner, for a plurality of pixels and a plurality of energy bins, correct the generated object scan data based on the calculated air scan correcting ratios, use the corrected object scan data to generate a line-integral sinogram, based on the obtained calibration table, and reconstruct the image of the imaging object, based on the generated line-integral sinogram.

(13) The apparatus of (11), wherein the processing circuitry is further configured to: obtain calibration air scan data and calibration slab scan data stored in the calibration data storage, wherein the calibration air scan data is generated through a calibration air scan performed during the calibration procedure, and the calibration slab scan data is generated through a calibration slab scan performed during the calibration procedure, calculate, based on the obtained calibration air scan data and the acquired air scan data, an air scan correcting ratio in a pixel-by-pixel, energy-bin-by-energy-bin manner, for a plurality of pixels and a plurality of energy bins, correct the obtained calibration slab scan data based on the calculated air scan correcting ratios, generate a calibration table based on the obtained calibration air scan data and the corrected calibration slab scan data, use the generated object scan data to generate a line-integral sinogram, based on the generated calibration table, and reconstruct the image of the imaging object, based on the generated line-integral sinogram.

(14) The apparatus of (11), wherein the processing circuitry is further configured to: obtain calibration air scan data, calibration slab scan data, and a calibration table stored in the calibration data storage, wherein the calibration air scan data is generated through a calibration air scan performed during the calibration procedure, and the calibration slab scan data is generated through a calibration slab scan performed during the calibration procedure, calculate, based on the obtained calibration air scan data and the acquired air scan data, an air scan correcting ratio in a pixel-by-pixel, energy-bin-by-energy-bin manner, for a plurality of pixels and a plurality of energy bins, calculate, for each specific air scan correcting ratio of the calculated air scan correcting ratios, a corresponding attenuation scan correcting ratio, based on the specific air scan correcting ratio, the obtained calibration air scan data, and the obtained calibration slab scan data, correct the generated object scan data based on the calculated attenuation scan correcting ratios, use the corrected object scan data to generate a line-integral sinogram, based on the obtained calibration table, and reconstruct the image of the imaging object, based on the generated line-integral sinogram.

(15) The apparatus of (14), wherein the processing circuitry is further configured to: for each specific air scan correcting ratio of the calculated air scan correcting ratios, calculate an energy bin threshold drift for an energy bin corresponding to the specific air scan correcting ratio, based on a linear interpolation or a higher order polynomial function of the obtained calibration air scan data associated with the energy bin and an adjacent energy bin, and calculate, based on the calculated energy bin threshold drift and the obtained calibration slab scan data, the corresponding attenuation scan correcting ratio.

(16) The apparatus of (14), wherein the processing circuitry is further configured to: select, among respective calibration slab scan data generated through a plurality of calibration slab scans performed on a plurality of slabs that have different attenuation pathlengths, calibration slab scan data generated through a calibration slab scan performed on a specific slab that has an attenuation pathlength closest to an attenuation pathlength of the imaging object, as the obtained calibration slab scan data.

(17) The apparatus of (14), wherein during the calibration air scan, a tube current is applied such that a difference between a detector counting rate caused during the calibration air scan and a detector counting rate of the calibration slab scan is less than or equal to a predefined threshold, and the processing circuitry is further configured to set a tube current applied during the air scan, such that a difference between a detector counting rate caused during the air scan and the detector counting rate of the calibration slab scan is less than or equal to the predefined threshold.

(18) The apparatus of (14), wherein the processing circuitry is further configured to: select, among respective calibration slab scan data generated through a plurality of calibration slab scans performed on a slab with a plurality of different tube currents applied, calibration slab scan data generated through a calibration slab scan with a specific tube current that is closest to a tube current applied in the object scan, as the obtained calibration slab scan data.

(19) The apparatus of (11), wherein the processing circuitry is further configured to: obtain calibration air scan data and calibration slab scan data stored in the calibration data storage, wherein the calibration air scan data is generated through a calibration air scan performed during the calibration procedure, and the calibration slab scan data is generated through a calibration slab scan performed during the calibration procedure, calculate, based on the obtained calibration air scan data and the acquired air scan data, an air scan correcting ratio in a pixel-by-pixel, energy-bin-by-energy-bin manner, for a plurality of pixels and a plurality of energy bins, calculate, for each specific air scan correcting ratio of the calculated air scan correcting ratios, a corresponding attenuation scan correcting ratio, based on the specific air scan correcting ratio, the obtained calibration air scan data, and the obtained calibration slab scan data, correct the obtained calibration slab scan data based on the calculated air scan correcting ratios, generate a calibration table based on the obtained calibration air scan data and the corrected calibration slab scan data, use the generated object scan data to generate a line-integral sinogram, based on the generated calibration table, and reconstruct the image of the imaging object, based on the generated line-integral sinogram.

(20) A non-transitory computer readable medium having instructions stored therein that, when executed by one or more processors, cause the one or more processors to perform a method for performing detector response correction in an X-ray imaging system having a photon-counting detector, the method comprising: obtaining calibration data stored in a calibration data storage, where the calibration data is generated during a calibration procedure performed with the X-ray imaging system at a first time; acquiring air scan data generated through an air scan performed with the X-ray imaging system at a second time, where the second time is after the first time; performing, with the X-ray imaging system, an object scan on an imaging object at a third time to generate object scan data, where the third time is after the second time; performing, using the generated object scan data, detector response correction based on the acquired air scan data and the obtained calibration data; and reconstructing, based on the performed detector response correction, an image of the imaging object.

Numerous modifications and variations of the embodiments presented herein are possible in light of the above teachings. It is therefore to be understood that within the scope of the claims, the disclosure may be practiced otherwise than as specifically described herein.

The invention claimed is:

1. A method for performing detector response correction in an X-ray imaging system having a photon-counting detector, the method comprising:

obtaining calibration data stored in a calibration data storage, where the calibration data is generated during a calibration procedure performed with the X-ray imaging system at a first time;

acquiring air scan data generated through an air scan performed with the X-ray imaging system at a second time, where the second time is after the first time;

performing, with the X-ray imaging system, an object scan on an imaging object at a third time to generate object scan data, where the third time is after the second time;

performing, using the generated object scan data, detector response correction based on the acquired air scan data and the obtained calibration data; and reconstructing, based on the performed detector response correction, an image of the imaging object, wherein the obtaining step further comprises obtaining calibration air scan data and a calibration table stored in the calibration data storage, wherein the calibration air scan data is generated through a calibration air scan performed during the calibration procedure, the step of performing the detector response correction further comprises:

calculating, based on the obtained calibration air scan data and the acquired air scan data, an air scan correcting ratio in a pixel-by-pixel, energy-bin-by-energy-bin manner, for a plurality of pixels and a plurality of energy bins, correcting the generated object scan data based on the calculated air scan correcting ratios, and using the corrected object scan data to generate a line-integral sinogram, based on the obtained calibration table, and the reconstructing step further comprises reconstructing the image of the imaging object, based on the generated line-integral sinogram.

2. The method of claim 1, wherein the acquiring step further comprises acquiring the air scan data generated through the air scan that is performed upon a predefined criterion being met, and the predefined criterion is met when a predefined time period has elapsed since the calibration procedure, when a difference between a condition under which the X-ray imaging system operates and the condition under which the calibration procedure is performed is larger than or equal to a predetermined threshold, and/or when a scan protocol to be applied with the X-ray imaging system is different from a scan protocol that is applied when the calibration procedure is performed.

3. A method for performing detector response correction in an X-ray imaging system having a photon-counting detector, the method comprising:

obtaining calibration data stored in a calibration data storage, where the calibration data is generated during a calibration procedure performed with the X-ray imaging system at a first time:

acquiring air scan data generated through an air scan performed with the X-ray imaging system at a second time, where the second time is after the first time:

performing, with the X-ray imaging system, an object scan on an imaging object at a third time to generate object scan data, where the third time is after the second time;

performing, using the generated object scan data, detector response correction based on the acquired air scan data and the obtained calibration data; and reconstructing, based on the performed detector response correction, an image of the imaging object, wherein the obtaining step further comprises obtaining calibration air scan data and calibration slab scan data stored in the calibration data storage, wherein the calibration air scan data is generated through a calibration air scan performed during the calibration procedure, and the calibration slab scan data is generated through a calibration slab scan performed during the calibration procedure, the step of performing the detector response correction further comprises:

calculating, based on the obtained calibration air scan data and the acquired air scan data, an air scan correcting ratio in a pixel-by-pixel, energy-bin-by-energy-bin manner, for a plurality of pixels and a plurality of energy bins, correcting the obtained calibration slab scan data based on the calculated air scan correcting ratios, generating a calibration table based on the obtained calibration air scan data and the corrected calibration slab scan data, and using the generated object scan data to generate a line-integral sinogram, based on the generated calibration table, and the reconstructing step further comprises reconstructing the image of the imaging object, based on the generated line-integral sinogram.

4. A method for performing detector response correction in an X-ray imaging system having a photon-counting detector, the method comprising:

obtaining calibration data stored in a calibration data storage, where the calibration data is generated during a calibration procedure performed with the X-ray imaging system at a first time;

acquiring air scan data generated through an air scan performed with the X-ray imaging system at a second time, where the second time is after the first time;

performing, with the X-ray imaging system, an object scan on an imaging object at a third time to generate object scan data, where the third time is after the second time;

performing, using the generated object scan data, detector response correction based on the acquired air scan data and the obtained calibration data; and reconstructing, based on the performed detector response correction, an image of the imaging object, wherein the obtaining step further comprises obtaining calibration air scan data, calibration slab scan data, and a calibration table stored in the calibration data storage, wherein the calibration air scan data is generated through a calibration air scan performed during the calibration procedure, and the calibration slab scan data is generated through a calibration slab scan performed during the calibration procedure, the step of the performing detector response correction further comprises:

calculating, based on the obtained calibration air scan data and the acquired air scan data, an air scan correcting ratio in a pixel-by-pixel, energy-bin-by-energy-bin manner, for a plurality of pixels and a plurality of energy bins, calculating, for each specific air scan correcting ratio of the calculated air scan correcting ratios, a corresponding attenuation scan correcting ratio, based on the specific air scan correcting ratio, the obtained calibration air scan data, and the obtained calibration slab scan data, correcting the generated object scan data based on the calculated attenuation scan correcting ratios, and using the corrected object scan data to generate a line-integral sinogram, based on the obtained calibration table, and the reconstructing step further comprises reconstructing the image of the imaging object, based on the generated line-integral sinogram.

5. The method of claim 4, wherein the step of calculating the corresponding attenuation scan correcting ratio further comprises:

for each specific air scan correcting ratio of the calculated air scan correcting ratios, calculating an energy bin threshold drift for an energy bin corresponding to the specific air scan correcting ratio, based on a linear interpolation or a higher order polynomial function of the obtained calibration air scan data associated with the energy bin and an adjacent energy bin, and calculating, based on the calculated energy bin threshold drift and the obtained calibration slab scan data, the corresponding attenuation scan correcting ratio.

6. The method of claim 4, wherein the obtaining step further comprises:

selecting, among respective calibration slab scan data generated through a plurality of calibration slab scans performed on a plurality of slabs that have different attenuation pathlengths, calibration slab scan data generated through a calibration slab scan performed on a specific slab that has an attenuation pathlength closest to an attenuation pathlength of the imaging object, as the obtained calibration slab scan data.

7. The method of claim 4, wherein during the calibration air scan, a tube current is applied such that a difference between a detector counting rate caused during the calibration air scan and a detector counting rate of the calibration slab scan is less than or equal to a predefined threshold, and the acquiring step further comprises setting a tube current applied during the air scan, such that a difference between a detector counting rate caused during the air scan and the detector counting rate of the calibration slab scan is less than or equal to the predefined threshold.

8. The method of claim 4, wherein the obtain step further comprises:

selecting, among respective calibration slab scan data generated through a plurality of calibration slab scans performed on a slab with a plurality of different tube currents applied, calibration slab scan data generated through a calibration slab scan with a specific tube current that is closest to a tube current applied in the object scan, as the obtained calibration slab scan data.

9. A method for performing detector response correction in an X-ray imaging system having a photon-counting detector, the method comprising:

obtaining calibration data stored in a calibration data storage, where the calibration data is generated during a calibration procedure performed with the X-ray imaging system at a first time;

acquiring air scan data generated through an air scan performed with the X-ray imaging system at a second time, where the second time is after the first time;

performing, with the X-ray imaging system, an object scan on an imaging object at a third time to generate object scan data, where the third time is after the second time;

performing, using the generated object scan data, detector response correction based on the acquired air scan data and the obtained calibration data; and reconstructing, based on the performed detector response correction, an image of the imaging object, wherein the obtaining step further comprises obtaining calibration air scan data and calibration slab scan data stored in the calibration data storage, wherein the calibration air scan data is generated through a calibration air scan performed during the calibration procedure, and the calibration slab scan data is generated through a calibration slab scan performed during the calibration procedure, the step of performing the detector response correction further comprises:

calculating, based on the obtained calibration air scan data and the acquired air scan data, an air scan correcting ratio in a pixel-by-pixel, energy-bin-by-energy-bin manner, for a plurality of pixels and a plurality of energy bins, calculating, for each specific air scan correcting ratio of the calculated air scan correcting ratios, a corresponding attenuation scan correcting ratio, based on the specific air scan correcting ratio, the obtained calibration air scan data, and the obtained calibration slab scan data, correcting the obtained calibration slab scan data based on the calculated air scan correcting ratios, generating a calibration table based on the obtained calibration air scan data and the corrected calibration slab scan data, and using the generated object scan data to generate a line-integral sinogram, based on the generated calibration table, and the reconstructing step further comprises reconstructing the image of the imaging object, based on the generated line-integral sinogram.

* * * * *